United States Patent [19]
D'Antonio et al.

[11] Patent Number: 5,589,639
[45] Date of Patent: Dec. 31, 1996

[54] SENSOR AND TRANSDUCER APPARATUS

[76] Inventors: Nicholas F. D'Antonio, 7695 Admiral Dr., Liverpool, N.Y. 13090; Nicholas J. D'Antonio, 138A Long Rd., Tully, N.Y. 13159

[21] Appl. No.: 182,578

[22] Filed: Jan. 18, 1994

Related U.S. Application Data

[63] Continuation-in-part of Ser. No. 621,653, Dec. 31, 1990, Pat. No. 5,279,163, which is a continuation-in-part of Ser. No. 834,939, Feb. 28, 1986, Pat. No. 4,823,619, and a continuation-in-part of Ser. No. 151,483, Feb. 2, 1988, Pat. No. 4,987,783.

[51] Int. Cl.$^6$ ............................................. G01L 9/00
[52] U.S. Cl. ......................... 73/724; 73/718; 128/661.08; 601/41
[58] Field of Search ........................... 73/379.02, 728, 73/745, 862.454, 862.585

[56] References Cited

U.S. PATENT DOCUMENTS

| | | |
|---|---|---|
| 4,066,054 | 1/1978 | Caron et al. ......................... 123/117 R |
| 4,399,606 | 8/1983 | Buckshaw . |
| 4,805,463 | 2/1989 | Kelledes et al. ........................ 7/862.331 |
| 4,823,619 | 4/1989 | D'Antonio et al. .................... 73/862.58 |
| 4,858,620 | 8/1989 | Sugarman et al. ......................... 73/172 |
| 5,279,163 | 1/1994 | D'Antonio et al. ................... 73/861.74 |

FOREIGN PATENT DOCUMENTS

| | | |
|---|---|---|
| 515114 | 3/1981 | Australia . |
| 2264464 | 10/1975 | France . |
| 731190 | 6/1955 | United Kingdom . |
| WO-A-8700951 | 2/1987 | WIPO . |
| 8700951 | 2/1987 | WIPO ............................ G08C 19/06 |

*Primary Examiner*—Richard Chilcot
*Assistant Examiner*—Ronald C. Biegel
*Attorney, Agent, or Firm*—D. Peter Hochberg; Mark Kusner; Michael Jaffe

[57] ABSTRACT

A force sensing system for a CPR device which generates an intelligible output signal corresponding to a force parameter. The system is comprised of a sensing device for sensing force exerted thereon and producing an electric reactance signal in response to the force exerted, and a processor for processing the electric reactance signal into an intelligible output signal which is shown on a display device.

2 Claims, 17 Drawing Sheets

C

RS1  RESET FOR CYCLE COUNTER

ST  STORAGE OF PARAMETER VALUE

RS2  RESET FOR PARAMETER COUNT

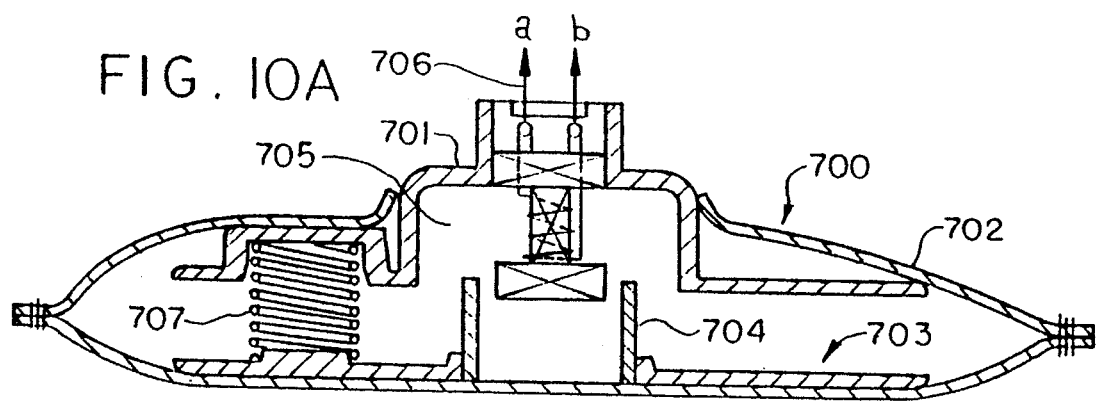
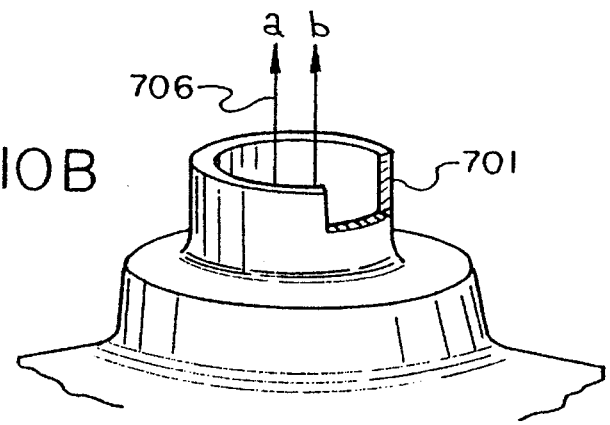
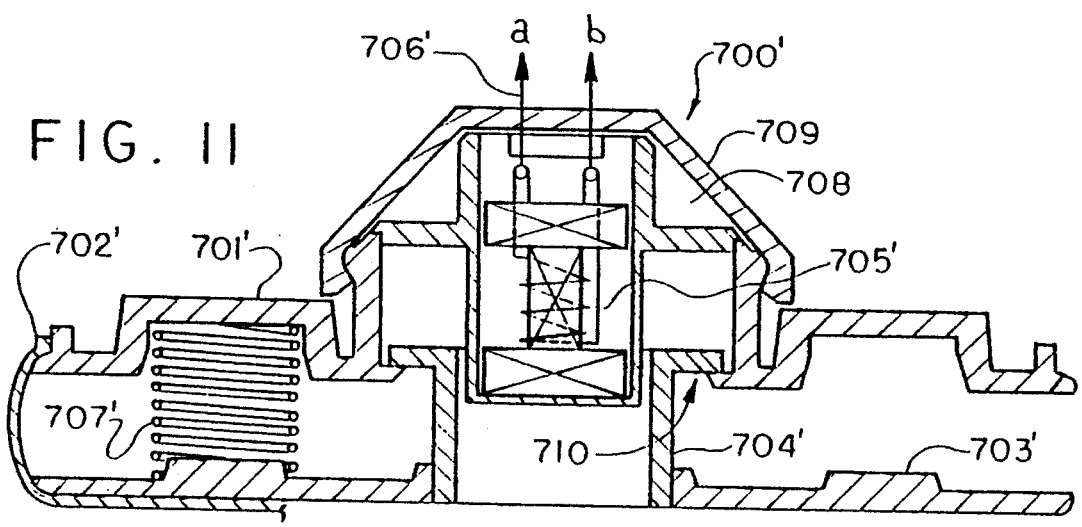

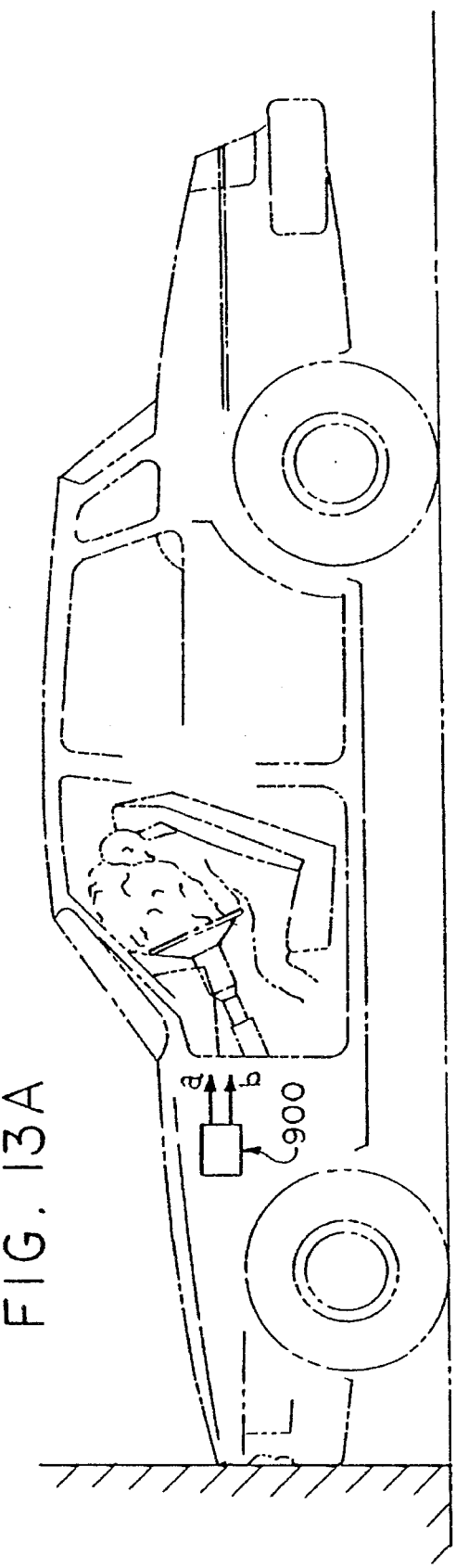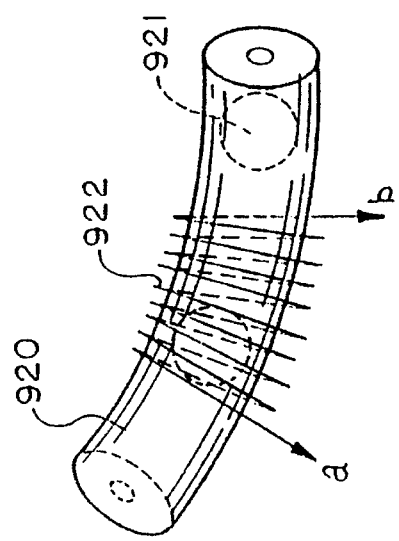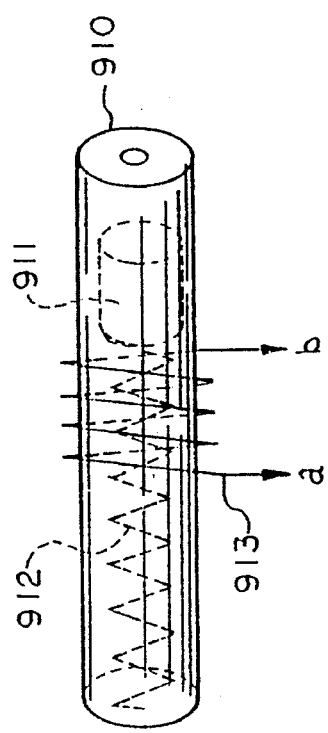

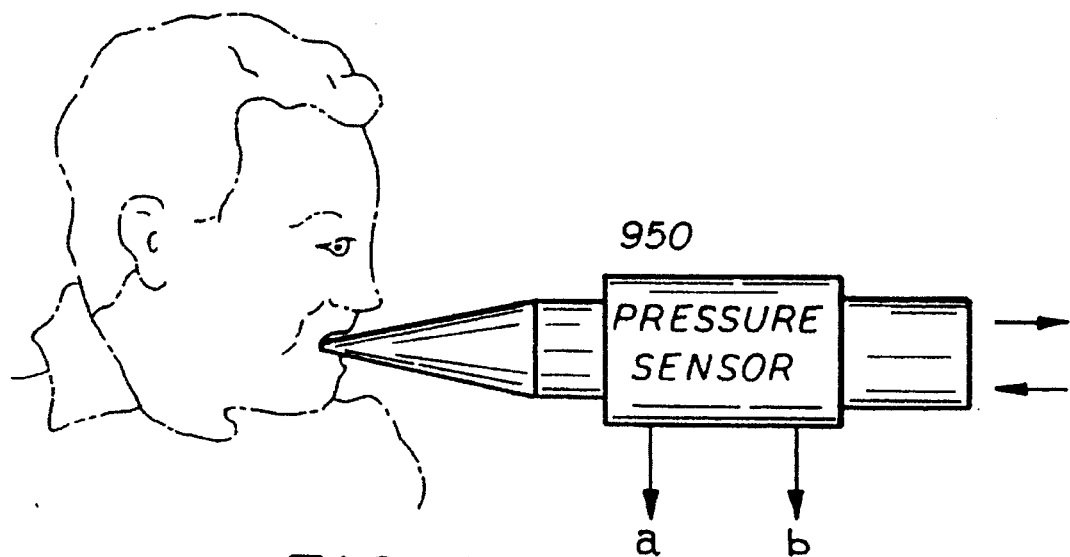
FIG. 14A
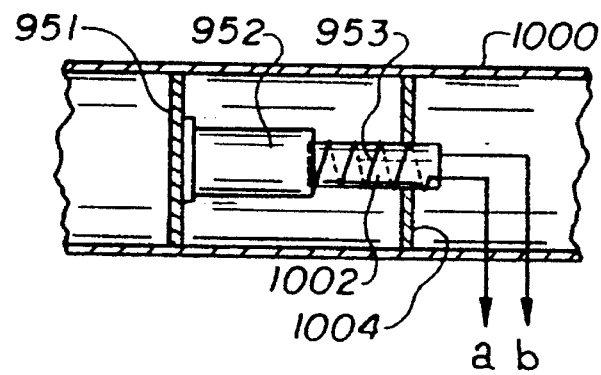
FIG. 14B1
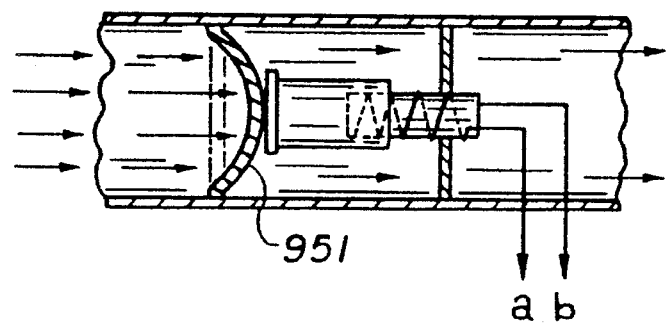
FIG. 14B2

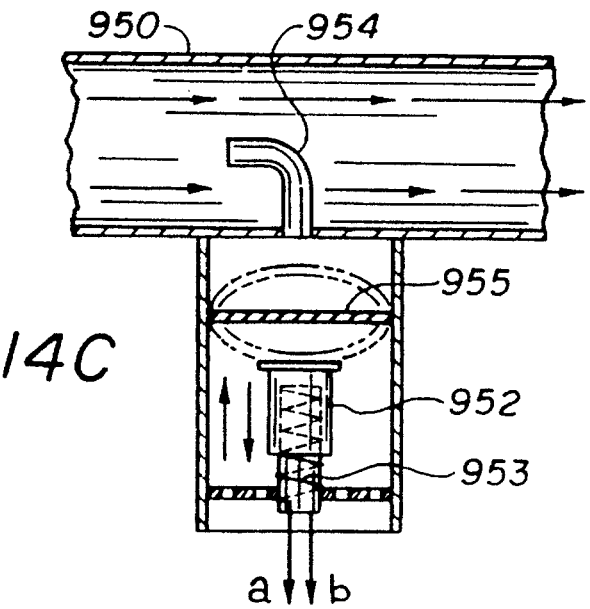
FIG. 14C
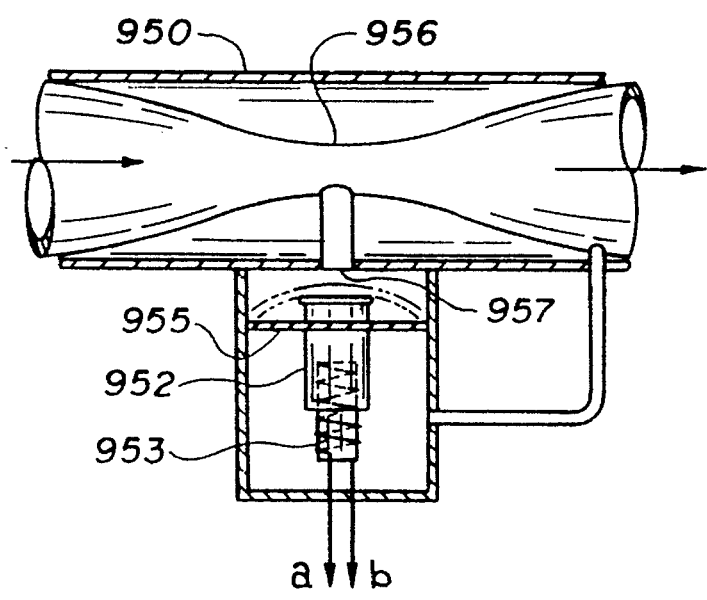
FIG. 14D
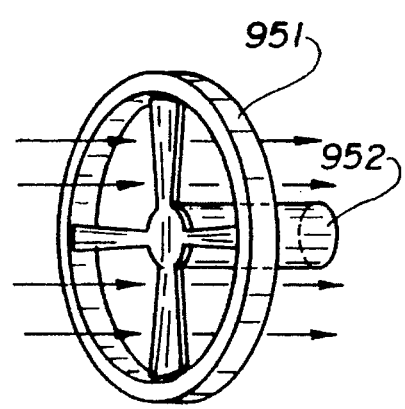
FIG. 14E1
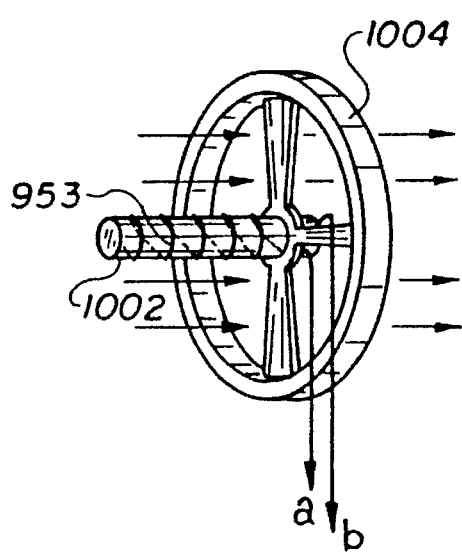
FIG. 14E2

SENSOR AND TRANSDUCER APPARATUS

This application is a continuation-in-part of application Ser. No. 07/621,653 filed on Dec. 3, 1990, now U.S. Pat. No. 5,279,163, for a "Sensor and Transducer Apparatus" by Nicholas F. D'Antonio and Nicholas J. D'Antonio, which is a continuation-in-part application Ser. No. 06/834,939, filed on Feb. 28, 1986, now U.S. Pat. No. 4,823,619, and of Ser. No. 07/151,483 filed Feb. 2, 1988 now U.S. Pat. No. 4,987,783.

BACKGROUND OF THE INVENTION

1. The Field of Invention

This invention relates generally to systems for sensing environmental or physical parameters such as for pressure, temperature and light changes, and to transducers for generating electrical signals corresponding to such remotely sensed environmental or physical parameters. The invention further relates to an electronically operated CPR force monitoring system.

2. State of the Art

A great many devices are known for sensing force and pressure values. For the purposes of the present discussion, the terms force and pressure can be considered interchangeable, and to include other force related values such as torque. Likewise, devices are known for sensing temperature and light parameter changes. Many of such devices are mechanical in nature, and many are electrical devices. While many of these devices have proven very effective for their intended uses, there remains a need in many areas for compact, reliable, effective, inexpensive and low power sensor and transducer devices and systems. For example, in U.S. Pat. No. 4,858,620, filed on Feb. 28, 1986 and which issued on Aug. 22, 1989, entitled "Warning Systems for Excessive Orthopedic Pressures", a non-invasive system for remotely monitoring the pressure beneath the cast on a part of the body is disclosed for warning when the measured pressure is approaching dangerous levels. That system should incorporate remote sensors which are compact enough to fit beneath the cast without requiring any modification to the cast's size or shape. Furthermore, the system, being battery operated and portable, must be reliable and effective to protect the patient, and still be of low power requirements and inexpensive. Although means are known for measuring pressures beneath casts, among the reasons why such means are not widely used are that they are invasive, difficult to use and their prohibitively expensive, particularly in view of the present absence of such systems in existing orthopedic procedures and because the addition of such systems would significantly increase the cost of the cast. Another medical application requiring a force detection system is a CPR unit in which the force applied to the lower sternum is displayed in real time for each of the cyclic compressions during the procedure. The object, of course, is to prevent forces that are too low to be effective or so high as to cause physical damage to the patient's chest.

Aside from the medical application discussed above, there are other applications where a need exists for low cost, remotely located sensors to be utilized in transducer circuitry. For example, such need exists in the automotive industry. This need is discussed by Flynn, in his article in *Product Engineering*, August, 1978 (pgs. 43–49).

A number of electrical devices have been developed and described in the patent literature for detecting changes in environmental or physical parameters. One such device is described in U.S. Pat. No. 4,552,028. This patent discloses a single device for measuring force by a capacitive sensor.

U.S. Pat. No. 4,562,382 discloses a solid-state inverter including a multiple core transformer which is useful as a high frequency power source for use in connection with an electron discharge lamb.

In U.S. Pat. No. 4,381,506, a single unit transducer apparatus is disclosed. This apparatus provides an electrical signal which senses motion of a component, e.g., a movable ring about a magnetically conductive core. This apparatus is designed for coupling to internal combustion engines.

In U.S. Pat. No. 4,156,223, an improved positional transducer is disclosed which utilizes an elongated, hollow, cylindrical tube of a magnetically saturable material, a sensing wire that runs through the tube parallel to its elongated axis and a pair of elongated, generally rectangularly shaped magnets of opposite polarity which are closely positioned adjacent diametrically opposite exterior portions of the tube. A similar positional transducer is illustrated in U.S. Pat. No. 3,958,203; however, the '223 patent is an improved version of the transducer disclosed in this patent.

U.S. Pat. No. 4,122,427 discloses a motion monitor particularly useful for monitoring infant respiration. The monitor comprises an oscillator driving an ultrasonic wave generator, a receiver for ultrasonic echoes, a phase detector for detecting phase shift between the outputs of the detector and an oscillator, and means for recovering the respiration envelope from the output of the phase detector.

U.S. Pat. No. 3,140,475 discloses a device for position and motion indication. The device includes a primary coil and a secondary coil coaxially aligned in an end-to-end relation and electrically connected in series, with an A.C. supply connected across the primary coil and a signal readout device connected across both the primary and secondary coils in series relation.

In U.S. Pat. No. 3,020,527, a position indicating system which will indicate the position of a device at a location remote from a movable device is provided. More specifically, a telemetric system is disclosed that may be employed expeditiously with an elongated tube which tube may act as a pressure wall.

U.S. Pat. No. 3,001,183 also relates to position indicator systems for sliding magnetic sleeves which operate within a completely enclosed vessel. Specifically, a remote linear position indicator is disclosed that has a sensing element positioned within a tubular magnetic wall.

U.S. Pat. No. 2,284,364 discloses a tensiometer for measuring thread tension while the thread is passing through the measuring device at a high rate. This device was designed for use in the fiber and garment industries.

U.S. Pat. No. 3,142,981 discloses a transducer device for producing digital electrical signals to measure the magnitude of force applied to the force sensing element. The force sensing element includes a load ring, and a means for applying a force to cause a deformation of the load ring. The patent also discloses employing an oscillator to produce a stable frequency within the frequency range of the oscillator whose frequency varies with the force applied to the load ring.

U.S. Pat. No. 3,206,971 discloses a force measuring apparatus wherein a frequency determining part of an oscillator is coupled to a spring member. The resilient deformation of the spring member caused by the forces to be measured produces frequency changes in the oscillator corresponding in magnitude to the deformation.

U.S. Pat. No. 3,522,858 discloses a snow-depth measuring device which permits measurement of small changes in the pressure of a liquid contained in a factory sealed chamber between two parallel plates, one of which is exposed to the snow fall. Attached to the outer frame of the device is a pressure transducer comprising bellows, a core piece and a coil, all enclosed in a housing.

U.S. Pat. No. 3,727,606 discloses a device for providing continuous monitoring of human respiration and heart rate comprising a fluid-type mattress located in contact with the human and producing pressure signals in response to the breathing and heart rate. A pressure transducer is provided for interpreting the pressure signals for application to an electronic circuit, or visual or audible recognition of the signals.

U.S. Pat. No. 3,791,375 discloses a device for sensing and warning of excessive ambulation force. The device is designed to be worn on a human foot, and may be used during recovery from orthopedic surgery of the lower extremity. The device comprises a fluid-containing load cell which deflects and changes its volume in accordance with the amount of load thereon.

U.S. Pat. No. 4,175,263 discloses a technique for monitoring the movement of an individual from a particular area. The device comprises a sealed fluid filled pad and comprises two distinct fluid areas or pressure sensing areas. Movement of a patient or a child is detected by the change in force or pressure exerted on the fluid.

U.S. Pat. No. 4,208,918 discloses a digital pressure sensor in which a first oscillator is associated with the pressure detector and a second oscillator of the same construction as the first is provided for determining a sampling period of the output signal of the first oscillator.

U.S. Pat. No. 4,324,259 discloses a device for detecting body function changes such as respiration and contractions of a woman in advanced pregnancy and labor. The device comprises a detector capsule having one wall defined by a resilient diaphragm for engagement with the abdominal wall and is connected to a variable volume compartment operably connected to a volume responsive transducer.

German Patent 737,882 discloses a position indicator which includes a movable magnetic sleeve about a core element containing longitudinal windings to vary inductance.

None of these above disclosures, however, teach or suggest the sensing means of the present invention. Also, a remotely located sensor from the transducing means of the type disclosed in the present application is not suggested by the teachings of the above discussed disclosures.

Other applications for pressure and the like monitoring systems, which might well be fulfilled upon the availability of compact, reliable, effective low power, portable and inexpensive remote sensors and associated transducer functions, involve measuring sport related values (e.g., measuring force applied to boxing gloves, boxing bags and running shoes; measuring total energy expended in bicycling; monitoring pressure in ski bindings and ski boots; measuring muscular expansion in a weight lifter); measuring the redistribution of body fluids in space or when subjected to varying and/or extreme gravitational forces; measuring weight; measuring pneumatic tire pressure, etc. Also, such a monitoring system may be useful for the remote monitoring of pressurized containers, e.g., fire extinguishers and gas containers used with analytical instruments and the like, respiration therapy, automotive performance, and monitoring fluid flow and fluid levels in industrial processes, to name a few.

SUMMARY OF THE INVENTION

It is an object of the present invention to provide an inexpensive pressure sensor.

Another object is to provide a pressure, temperature and/or light sensor which is compact.

A further object is to provide a pressure, temperature and/or light sensor, which is reliable and durable.

The provision of sensing systems for sensing environmental or physical parameters and for providing signals reflective of the value of those parameters at remote locations, is another object of the invention.

Another object is to provide a sensing system for generating an intelligible output signal corresponding to an environmental or physical parameters at a location remote from the place where the parameters is sensed.

Still another object is the provision of a compact, inexpensive, low power and accurate sensing means for generating electric signals for transmission to a remote processor.

Another object of the present invention is to provide a sensor and transducer system which can be used to measure and display forces such as the force applied to the sternum during the CPR procedure. The technique is applicable to portable devices for use in emergency situations removed from a clinical setting or for use with more stationary equipment in hospitals or trauma centers.

Another object of the present invention is to provide a sensor and transducer system that is applicable to a wide variety of uses, while being inexpensive, reliable, compact, durable and low power.

Other objects will be apparent from the description to follow and from the appended claims.

The foregoing objects are achieved according to preferred embodiments of the invention by the provision of a sensing system for generating output signals according to the value of a sensed environmental or physical parameter, the system having sensing means composed of relatively movable electrical members which generate electric reactance signals corresponding to the value of the environmental or physical parameter. The reactant signal is transmitted to a processor having a CMOS Schmitt trigger logic inverter oscillator which receives the signal and generates a corresponding transduced signal for further processing to yield the output signal. The sensing device is preferably composed of an inductor coil mounted on a supporting member, and a second inductor element movable relative to the coil for generating an inductance signal corresponding to the value of the sensed parameter. The sensing device can alternatively be composed entirely of resistive or capacitive elements whose output is reflected by a reactance response in the oscillator, wherefore, the output of the sensing device is broadly described as a reactance signal. Various specific structures of the foregoing components are provided according to the application to which the inventive concepts are employed.

According to the preferred embodiments described below, a CPR compressive force monitoring system includes a section for being placed on the sternum of a victim. Compressive manual force is applied to the section. The force is monitored so that it can be held within safe and effective values. The monitor or force sensing system has a stationary position and a movable portion for generating an electrical reactance signal according to the applied force. A force dependent oscillator generates a signal whose frequency corresponds to the force, and a frequency-to-voltage converter generates a voltage signal corresponding to the applied force. Comparators receive the voltage signal and generate a comparator outlet signal corresponding to the magnitude and change of the applied force. An electronic (such as an LCD) or mechanical display reveals an intelligible output signal on indicators showing force values.

BRIEF DESCRIPTION OF THE DRAWINGS

FIGS. 10(A) and 10(B) are, respectively, a cross-section and a detailed partial perspective view of a sensor pad or sensing device according to another embodiment of the invention.

FIG. 11 is a cross-section and a detailed partial perspective view of another embodiment of the sensor pad illustrated in FIG. 10.

FIG. 13(A) is a schematic view of a sensing system according to the invention for controlling the operation of an air bag in a motor vehicle.

FIGS. 13(B) and 13(C) are perspective views of variations of an embodiment of a sensing device according to the invention for generating an inductance signal corresponding to a sensed acceleration.

FIG. 14(A) illustrates an embodiment of the present invention used in combination with a respiratory spirometer. FIGS. 14(B1), 14(B2) (D) are detailed partial cross-sectional views of embodiments of the apparatus shown in FIG. 14(A), and FIG. 14(E1), 14(E2) is a perspective view of an air flow intercepting flexible diaphragm.

The invention will be further described in connection with the attached drawing figures showing preferred embodiments of the invention including specific parts and arrangements of parts. It is intended that the drawings included as a part of this specification be illustrative of preferred embodiments of the invention and should in no way be considered as a limitation on the scope of the invention.

DETAILED DESCRIPTION OF THE PREFERRED EMBODIMENT

Figure 1:
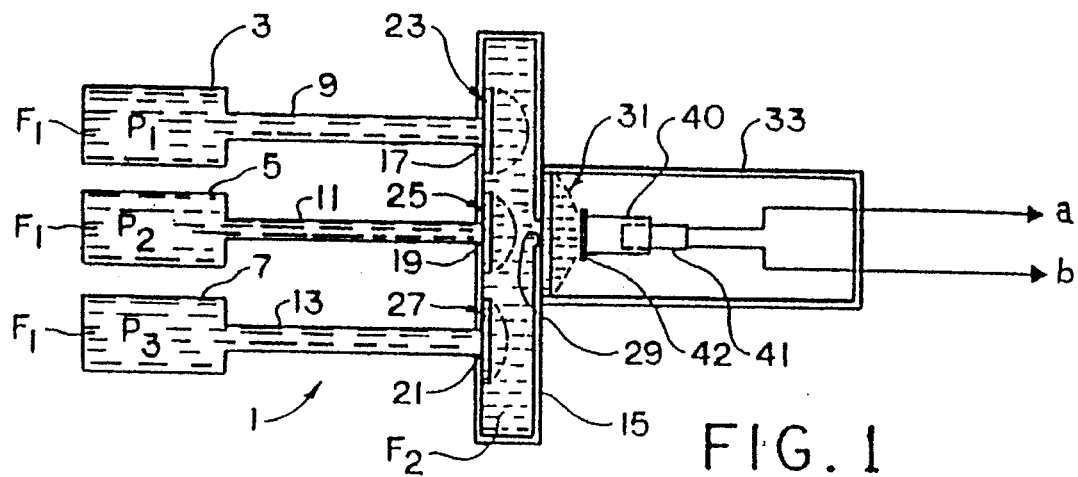
FIG. 1 is a schematic diagram of a sensor system according to a preferred embodiment of the invention for indicating the sum of a number of sensed pressures and illustrating a reluctance type remote sensor.

Referring first to FIG. 1, a sensor system 1 is shown composed of a number of compressible pads 3, 5 and 7 connected respectively by conduits 9, 11 and 13 to a fluid container 15. Although only three pads are shown, any number N of pads can be used. The pads and their respective conduits are filled with a fluid $F_1$, which can be a gas such as air, but for most applications is preferably an incompressible liquid. However, the fluid is preferably a gas if a change in temperature is to be measured, for example, in a temperature controlled heated glove, boots, face mask or other wearing apparel or other apparatus or regions, such as the temperature build up trapped beneath the surface of a newly applied cast, which if undetected, can cause further injury and pain to the patient. The pads 3, 5 and 7 enter reservoir 15 through ports 17, 19 and 21 respectively. A diaphragm 23 extends over port 17 to isolate the volume of pad 3 and conduit 9 from container 15. Diaphragms 25 and 27 similarly seal off pad 5 and conduit 11, and pad 7 and conduit 13, respectively. Fluid $F_1$ thus fills each pad, its connecting conduit, and the region within the diaphragm associated with the respective conduits. A port 29 is provided in reservoir 15, and a transducer diaphragm 31 extends over port 29, the latter diaphragm being disposed in a casing 33. A displaceable deflection transfer means in the form of a second fluid $F_2$, which fills the volume between diaphragms 23, 25, 27 and 31 (i.e., essentially filling reservoir 15), controls the flexing of diaphragm 31. Fluid $F_2$ may be the same as, or different from, fluid $F_1$. A tubular ferromagnetic shield or cap 40 is attached to diaphragm 31, for movement over an inductor coil 41 in a telescoping manner. The output of transducer diaphragm 31, providing an inductive change in coil 41 as shield 40 moves over coil 41. The output of coil 41 is shown by the arrows a, b. Outputs a and b are connected to a circuit for changing the frequency of an oscillator circuit, as the one described below in FIG. 5.

When pressure is exerted on any or all of pads 3, 5 and 7, as indicated by the pressure values P1, P2 and P3, fluid $F_1$ moves through the respective conduits 9, 11 and 13 and effects an expansion of the respective diaphragms 23, 25 and 27. When not deflected, the diaphragms are attached tightly over the respective ports 17, 19 and 21 (as shown by the solid lines) to assure an accurate and detectable response to pressures P1, P2 and/or P3. FIG. 1 shows a situation where P1 is greater than P2, and P2 is greater than P3, wherefore the deflection of diaphragm 23 exceeds that of diaphragm 25, which exceeds that of diaphragm 27. The diaphragms in their deflected states are shown in dashed lines. The effective flow areas of conduits 9, 11 and 13 should be very narrow, to get a relatively large fluid movement and diaphragm deflection for even minute pressure changes on the pad.

The expansion of diaphragms 23, 25 and 27 exerts pressure on fluid $F_2$, and this in turn effects an expansion of transducer diaphragm 31 (from its solid position to its dashed line portion) according to the sum of the deflection of diaphragms 23, 25 and 27, to yield a corresponding electrical parameter change a, b. This parameter change results from the movement of cap 40 attached to diaphragm 31 at interface 42 over coil 41. The variable impedance produced as a result of the movement of diaphragm 31 changes, in this instance, the reluctance of coil 41 to change $Z_1$ in FIG. 5.

Figure 15:
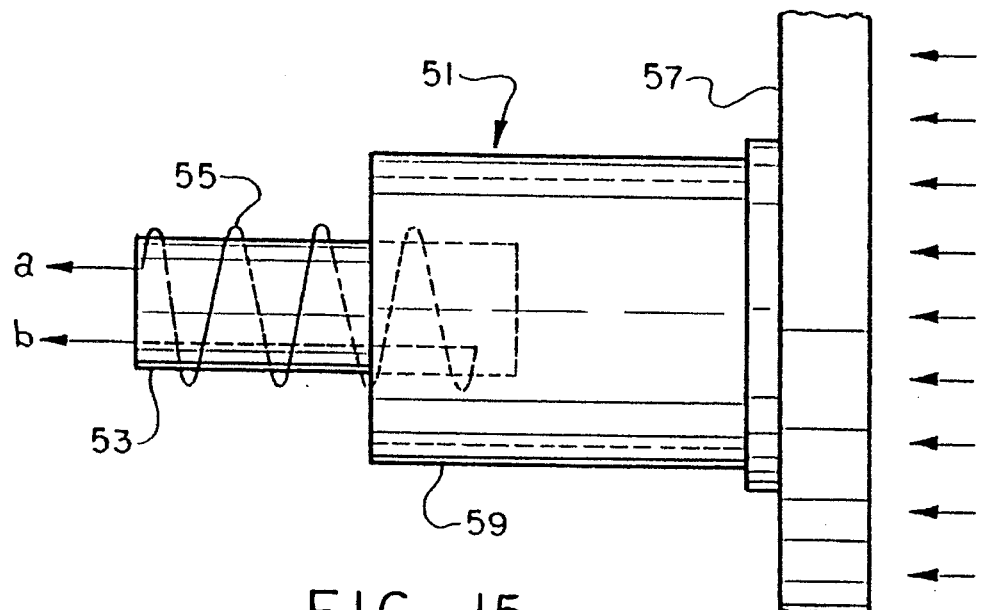
FIG. 15 illustrates a cross-section of a sensing device which can be incorporated in embodiments of the invention, such as in the remote sensors of FIGS. 1, 2, 3, 10, 11, 12, 13 or 14.

Referring at this juncture to FIG. 15, a reluctance transducer 51 which could be used to fulfill the functions of shield 40 and coil 41 is shown. This device is described in detail in U.S. Pat. No. 607,654 filed May 7, 1984 (attorney's docket 8943). Transducer 51 includes a core 53 about which a coil 55 is wound. Preferably core 53 and coil 55 are rigidly mounted with respect to a flexible diaphragm 57 on which a hollow cylinder 59 is securely mounted. Core 53 is preferably made of a ferromagnetic material to increase the inductance of coil 55. Hollow cylinder 59 can be a non-ferrous metallic or ferromagnetic material whose relative position will variably alter the magnetic field around the coil, allowing for either an eddy current or altered magnetization effect. As shown in FIG. 15, core 53 and coil 55 protrude partially into hollow cylinder 59. In response to forces applied to the diaphragm (in the horizontal direction according to the drawing of FIG. 15), diaphragm 57 flexes with the result that the coil is inserted further into or withdrawn from cylinder 59. When current flows through coil 55, a corresponding magnetic field is created around the coil. Part of that field is intercepted by cylinder 59 and is modified by the cylinder. As diaphragm 57 flexes, more or less of the magnetic field of coil 55 is intercepted, resulting in a change with respect to time of the current flowing through coil 55. This time rate of change of current and its corresponding field is a direct result of the inductive changes within coil 55 by virtue of the variable reluctance provided with the movement of cylinder 59 in the region about coil 55. The output a-b of device 51 applies on the ends of the conductor forming coil 55, and is transmitted to the processing unit of FIG. 5 to change the value of $Z_1$ therein.

The shape of coil 55 in FIG. 15 is merely schematic. The coil need not be helical and could even be planar. Various coil configurations and the choice of core and shield materials affect the basic inductance achievable and the magnitude of the changes in inductance, i.e., the dynamic range and sensitivity of the transducer resulting from the relative motion of the elements of the transducer. However, so long as the movement of the diaphragm is linear with respect to the applied force and the reluctance means principally intercepts relatively straight magnetic lines, the response of the transducer is linear.

A number of examples of the embodiment of FIG. 15 have been constructed and their electrical characteristics measured. Core 53 was formed from a ferromagnetic material and coil 55 would around it. In these examples, cylinder 59 has a close fit over coil 55 but is relatively free from physical contact in order to reduce the friction between them to a minimum. A plastic sleeve was placed over the coil to protect it against damage and to reduce that friction. In general, a closer fit between the cylinder and coil yields a greater dynamic range but a greater risk of friction; a looser fit yields a smaller dynamic range and a lower risk of friction. It was desired to construct a small, low cost, light weight transducer so cylinder 59 was constructed of aluminum in the measured examples. In order to obtain linear operation in any embodiment, it is preferable to have the edge of cylinder 59 intercept only the magnetic lines created by coil 55 that are nearly parallel to the longitudinal axis of core 53. In terms of the dimensions of the measured examples, the edge of cylinder 59 should extend over and cover a portion of the coil beyond the end of core 53 during operation to assure operation in the linear range. In the measured examples, diaphragm 57 was initially a convoluted rubber diaphragm having a central planar surface with concentric corrugations between it and the outer support structure. However, this type of diaphragm was found subject to drift, i.e., gradual position changes or "creep" under the influence of a steady state pressure or force. The drift effect is greatly reduced if a soft spiral spring is used in conjunction with the diaphragm. Furthermore, in that the spring provides increased resistance to its movement, spring strength is used to design for the desired force or pressure range to be measured. A different diaphragm was constructed with a circular piece of flat or "sheet" rubber stretched over an open ended cylinder. This arrangement provides the necessary stability for very small pressures without the use of the enhancement spring mentioned above.

Figure 16:
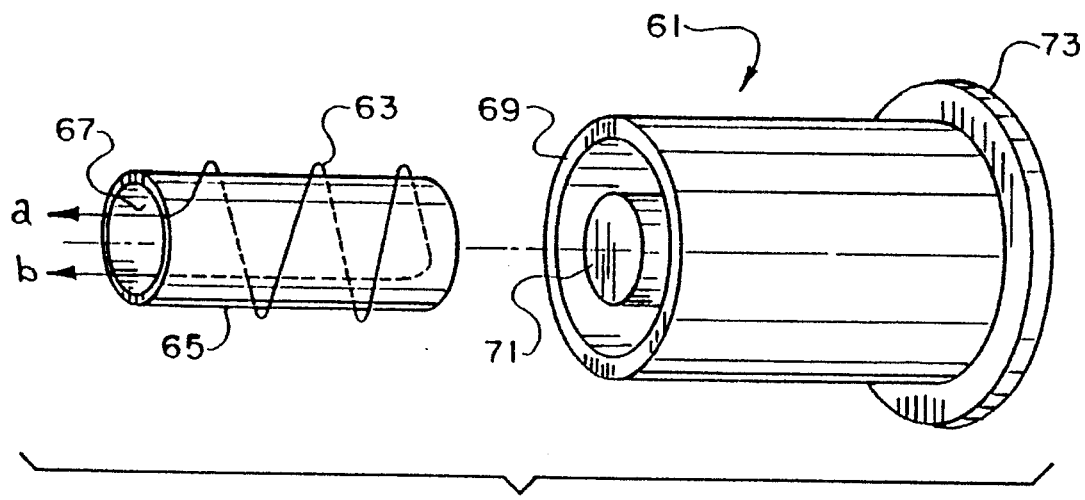
FIG. 16 illustrates a cross-section of another type of sensing device which can be used in embodiments of the present invention, such as the embodiments of the remote sensor of FIGS. 1, 2, 3, 10, 11, 12, 13 or 14.

Another type of reluctance transducer is shown as device 61 in FIG. 16. There a coil 63 is wound around a tubular structure 65 which has an air inner core 67. The reluctance shield includes a tubular portion 69 which is concentric to rod 71. While these elements are shown separated in FIG. 16 for clarity, in use core 65 is received by tubular shield 69 and rod 71 is received by air core 67. Both tube 69 and rod 71 are mounted on a flexible diaphragm 73 to which the forces to be measured are applied. In comparison to the embodiment of FIG. 15, this embodiment yields a lower inductance because of air core 67, but a greater dynamic range because a large portion of the total magnetic field produced by coil 63 is influenced by the incremental movement of the shield 69 and rod 71 over and into the coil. A very useful alternative to the simultaneous movement of tube 69 and rod 71 over an into the coil, is to securely mount tube 69 around the outer portion of coil 63. As a stationary shield, tube 69 will protect the coil against outside disturbances such as magnetic or electro-magnetic field or the motion of other metallic parts in the vicinity of the measurement. In this case, only the inner tube 71 will move into or out of the core section of the coil, i.e., a reversal of the means shown in FIG. 15. Shield 69 can be a ferromagnetic material for best results in this approach.

Returning now to FIG. 1, diaphragm 31 should be attached loosely over port 29 to assure an easy deflection of diaphragm 31 in response to deflections of diaphragms 23, 25 and 27 and to minimize the back pressure or resistance to such deflection in diaphragm 31. Also, each of diaphragms 23, 25, 27 and 31 should be secured as closely as possible to the ports over which they extend to prevent reverse deflection if the pressure in any of the pads is zero while that of a neighboring pad is greater than zero. Accordingly, with each of the pads isolated from the other, any pad may be disconnected from container 15, with no adverse effect on the operation of the remaining pads. The average of pressures P1, P2 and P3 is simply obtained by dividing the total pressure detected by the number of pads and associated diaphragms—in this case 3. This can be done electronically as pointed out below.

Figure 2:
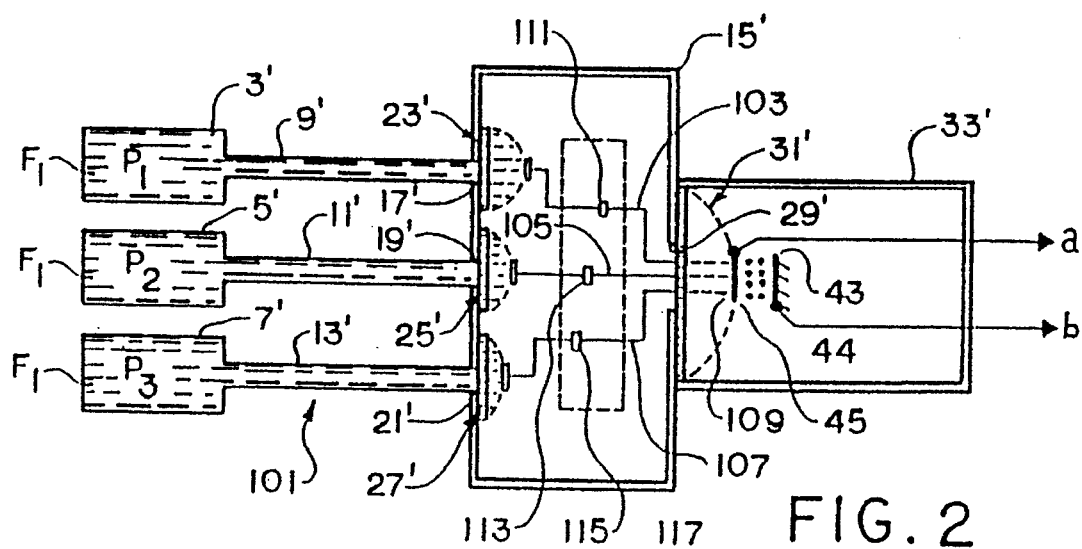
FIG. 2 is a schematic diagram of a sensor system according to a preferred embodiment of the invention for indicating the maximum value of a number of sensed pressures and illustrating a resistive type remote sensor.

Turning next to FIG. 2, a sensor system 101 for measuring the maximum of a number of sensed pressures is shown. Ports corresponding to ports in system 1 of FIG. 1 have been ascribed corresponding reference numbers, but with a prime (') suffix. Thus, system 101 includes pads 3', 5' and 7' connected respectively by conduits 9', 11' and 13' to a container 15' through ports 17', 19' and 21'. Diaphragms 23', 25' and 27' extend over the foregoing ports. Fluid fills the respective pad-conduit-diaphragm arrangements to form three independent, closed fluid subsystems.

Unlike reservoir 15, container 15' is not filled with fluid. The displaceable deflection transfer means are in the form of pushrods 103, 105 and 107, which are connected respectively at one end to diaphragms 23', 25' and 27' and at their respective opposite ends to diaphragm 31'. A contact region 109 is the place where the pushrods contact diaphragm 31'. When pressures P1, P2 and P3 are applied to pads 3', 5' and 7', only the pushrod attached to the diaphragm having the greatest deflection contacts and moves diaphragm 31'. The amount of movement of diaphragm 31' is a measure of the maximum value of the pressures P1, P2 and P3, and determines the electrical parameter change a, b.

The electrical parameter change is illustrated as a resistive parameter in this figure. A conductive plate 43 is mounting in a fixed position opposite a conductive plate 45 which is movable with diaphragm 31'. Sandwiched between conductive plates 43 and 45 is a variable resistance interface 44. As diaphragm 31' is deflected, plate 45 moves toward stationary plate 43 and thus changes the gap between the plates which, in turn, varies the signal transmitted by a, b. The variable resistance can be a fluid or a dry control media.

A set of pushrods 103, 105 and 107 interconnect diaphragms 23', 25' and 27' at one of their ends, and diaphragms 31' at their other ends. Pushrods 103, 105 and 107 have pressure markers 111, 113 and 115. A window 117 is provided in housing 15' through which the pressure markers are visible so that one can observe the respective pad pressures. FIG. 2 shows a situation where P1 exceeds P2 and P3, so that only pushrod 103 deflects transducer diaphragms 31'. It would be advantageous for diaphragms 23', 25' and 27' to be arranged in a triangular cluster so that each of pushrods 103, 105 and 107 can have the same length and shape.

The pushrods can be replaced with individual transducers at each of diaphragms 23', 25' and 27' (as indicated hereinafter), and this arrangement can be used to find the sum, average or maximum pressure by processing the signals electronically.

Figure 3:
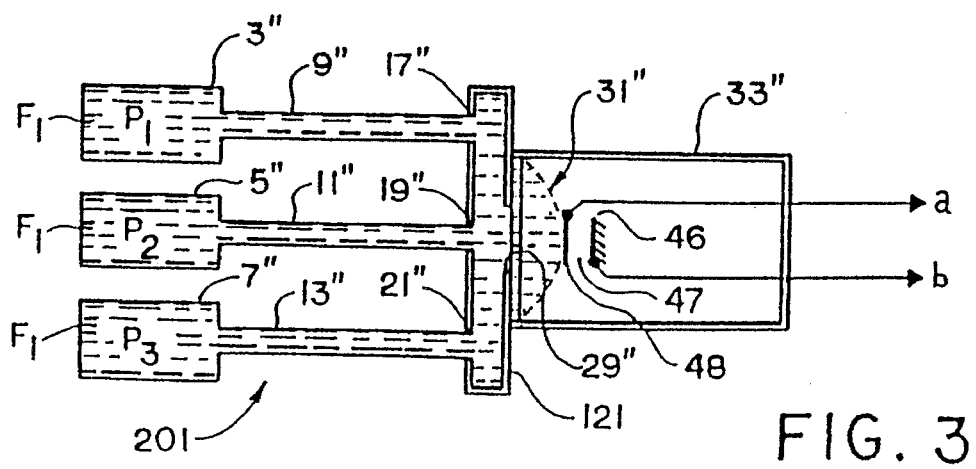
FIG. 3 is a schematic diagram of a sensor system according to a preferred embodiment of the invention for indicating the cumulative or average value of a number of sensed pressures and illustrating a capacitive type remote sensor.

Referring next to FIG. 3, a sensor system 201 is shown for measuring the sum of a number of sensed pressures. As with regard to FIG. 2, parts of system 201 corresponding to parts of system 1 in FIG. 1 have been described by corresponding reference numbers with double prime C) suffixes. Thus, system 201 includes pads 3", 5" and 7" from which extend conduits 9", 11" and 13" respectively. The conduits are connected to a common fluid chamber 121 through ports 17", 19" and 21". A port 29" is also provided in chamber 121, and transducer diaphragm 31" extends over port 29". Fluid $F_1$ is thus confined in the volume defined by pads 3", 5" and 7", conduits 9", 11" and 13", chamber 121 and the space under diaphragm 31" in housing 33". The pressures P1, P2 and P3 applied to pads 3", 5" and 7" are reflected as a common, cumulative pressure $P_{sum}$ in chamber 121 and throughout the fluid system, and $P_{sum}$ is reflected in the deflection of diaphragm 31" and in the value of electrical parameter change a, b. This is a particularly accurate arrangement when the pads are situated in a thoroughly restricted environment where they cannot expand if another pad is compressed. The improved accuracy occurs because reverse pressure from diaphragm 31" cannot influence the deflection characteristics of the other diaphragms. The average can be obtained as described with respect to the structure of FIG. 1.

The electrical parameter change illustrated in this figure is capacitance. A pair of electrically conductive, relatively movable capacitor plates 46 and 48 are separated by nonconductive dielectric, shown here as an air interface 47. The deflection of diaphragm 31" results in movement of plate 48 toward stationary plate 46. Thus, the gap between the two plates decreases which, in turn, registers a change in capacitance at a and b, i.e., $Z_2$ in FIG. 5.

The construction of the fluid pads can be very important, particularly when small pressures are to be detected, such as on the order of 30 mm Hg or 0.58 psi. As noted earlier, the fluid for most applications should be a liquid. However, if the sensor arrangement according to the invention is to be used for detecting temperature such as for temperature compensation applications, or for the detection of uncomfortable or irritating temperature build-up in the confines of a newly applied cast, the fluid $F_1$ should be air or other gas.

When the fluid is liquid, it is preferable to use an anti-freeze liquid to avoid the damage which could result if freezing temperatures are encountered. It has been found that diaphragm associated with the respective pads deflect with elevation, in that the deflection increases as the pad is elevated above the diaphragm level. It has been found that by initially filling the pads with a fluid-saturated absorbent such as sponge from which excess fluid has been allowed to discharge, the diaphragm does not react to pad position or temperature, although the diaphragm does maintain a fine sensitivity to changes in pressure applied to the pad. That is, the fluid in the sponge or other absorbent is not affected by changes in position, expansion or contraction, but it reacts immediately by discharging fluid to the diaphragm compartment upon the slightest change in pressure.

Figure 4:
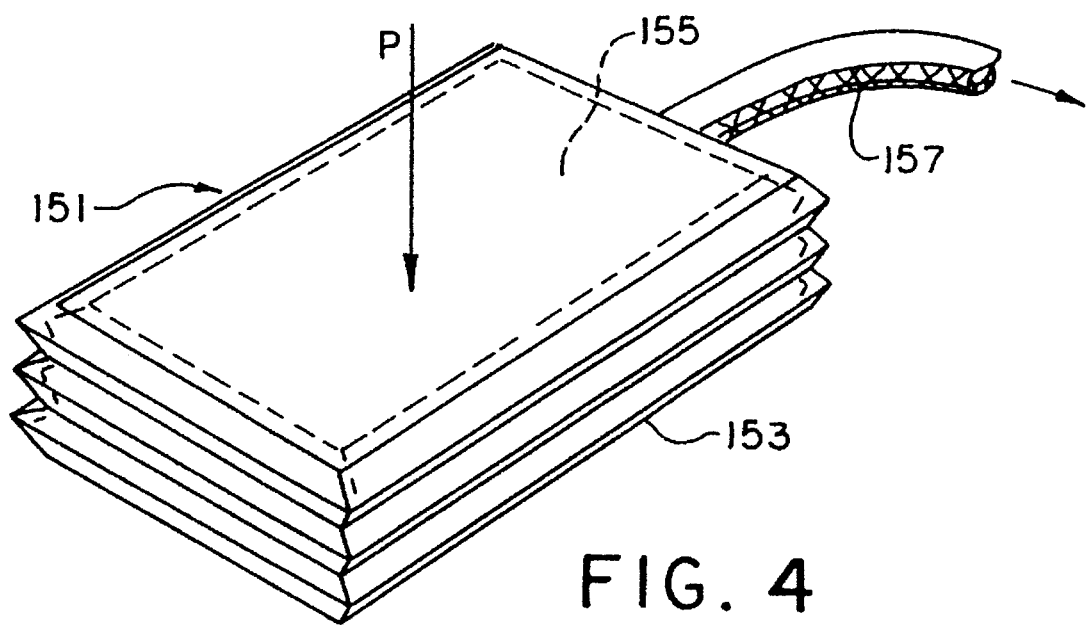
FIG. 4 is a perspective view of a sensor pad according to one embodiment of the invention.
Figure 17A:
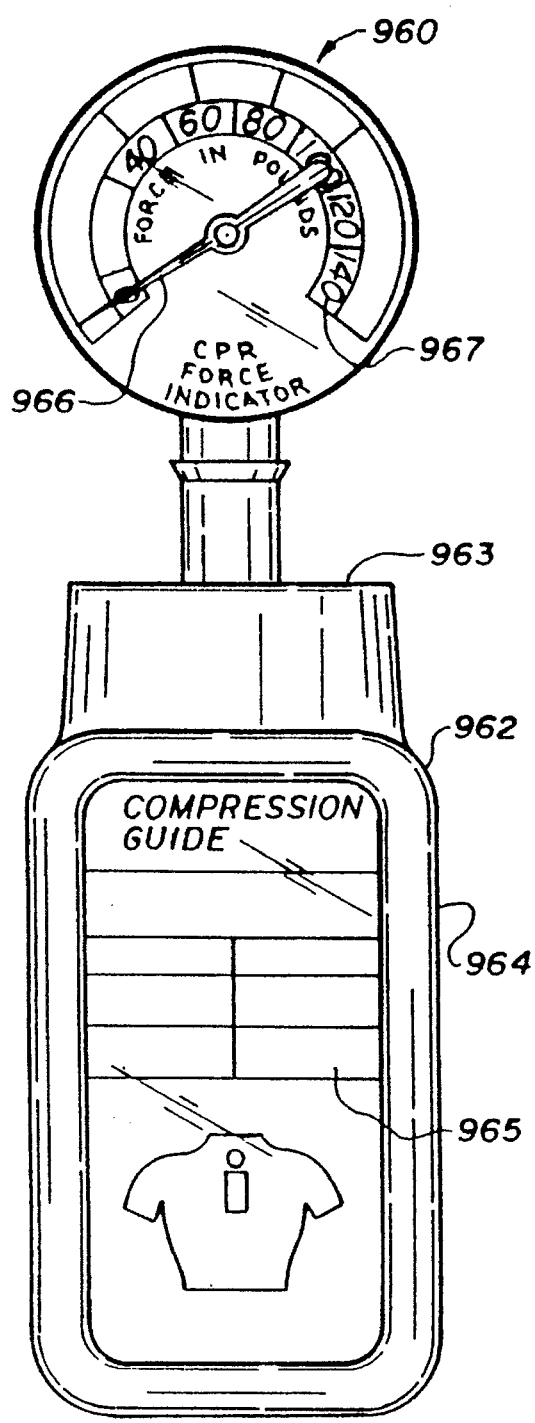
FIG. 17A illustrates a hand-held CPR unit with an electrically operated mechanical gauge.
Figure 17B:
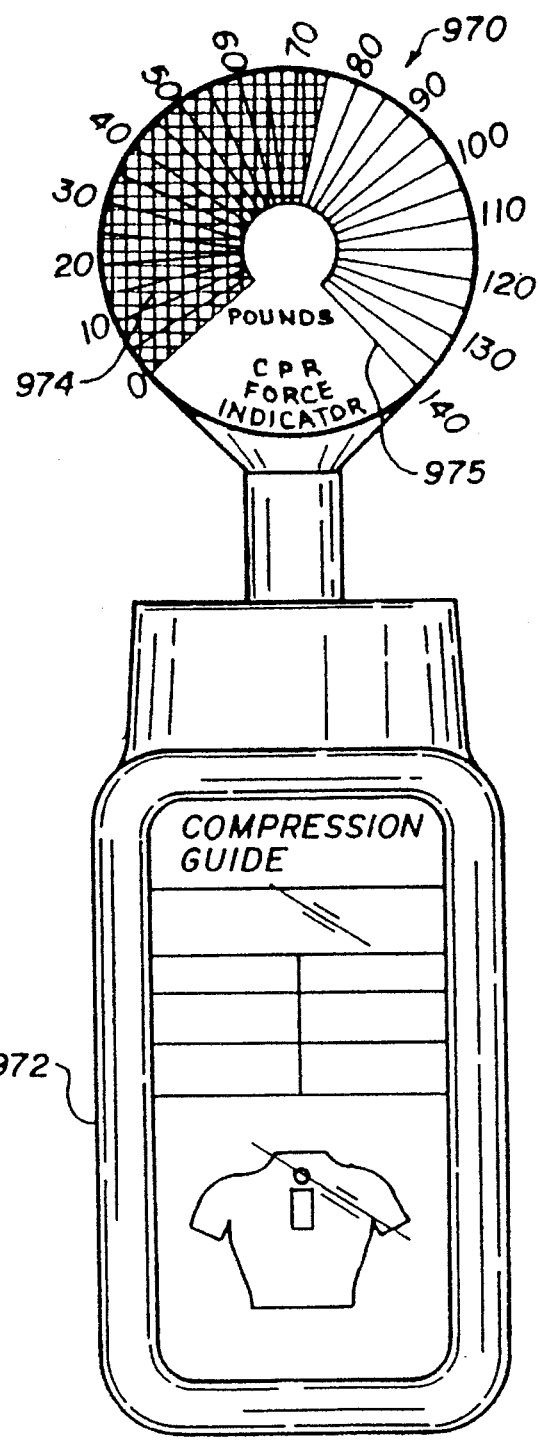
FIG. 17B illustrates an electronic version of the CPR device depicted in FIG. 17A, wherein the display is a radial LCD wherein the shaded portion illustrates an applied force of 75 pounds.

Finally, for many applications such as the CPR devices shown in FIGS. 17A and 17B, the pad should be soft and pliable, but it should resist stretching since fluid displacement must move into the conduit and against the diaphragm and not into an increased volume created by a stretched pad. Particularly satisfactory materials for the pads have been found to be polypropylene and thick walled latex tubing. Furthermore, a bellows type pad construction offers the desired resistance to stretch, while providing a thin profile, and a high response sensitivity. Such a construction is shown in FIG. 4, where a pad 151 has pleated side walls 153, a fluid saturated sponge 155 and a fluid conduit 157. The applied pressure is shown by arrow P.

Figure 5:
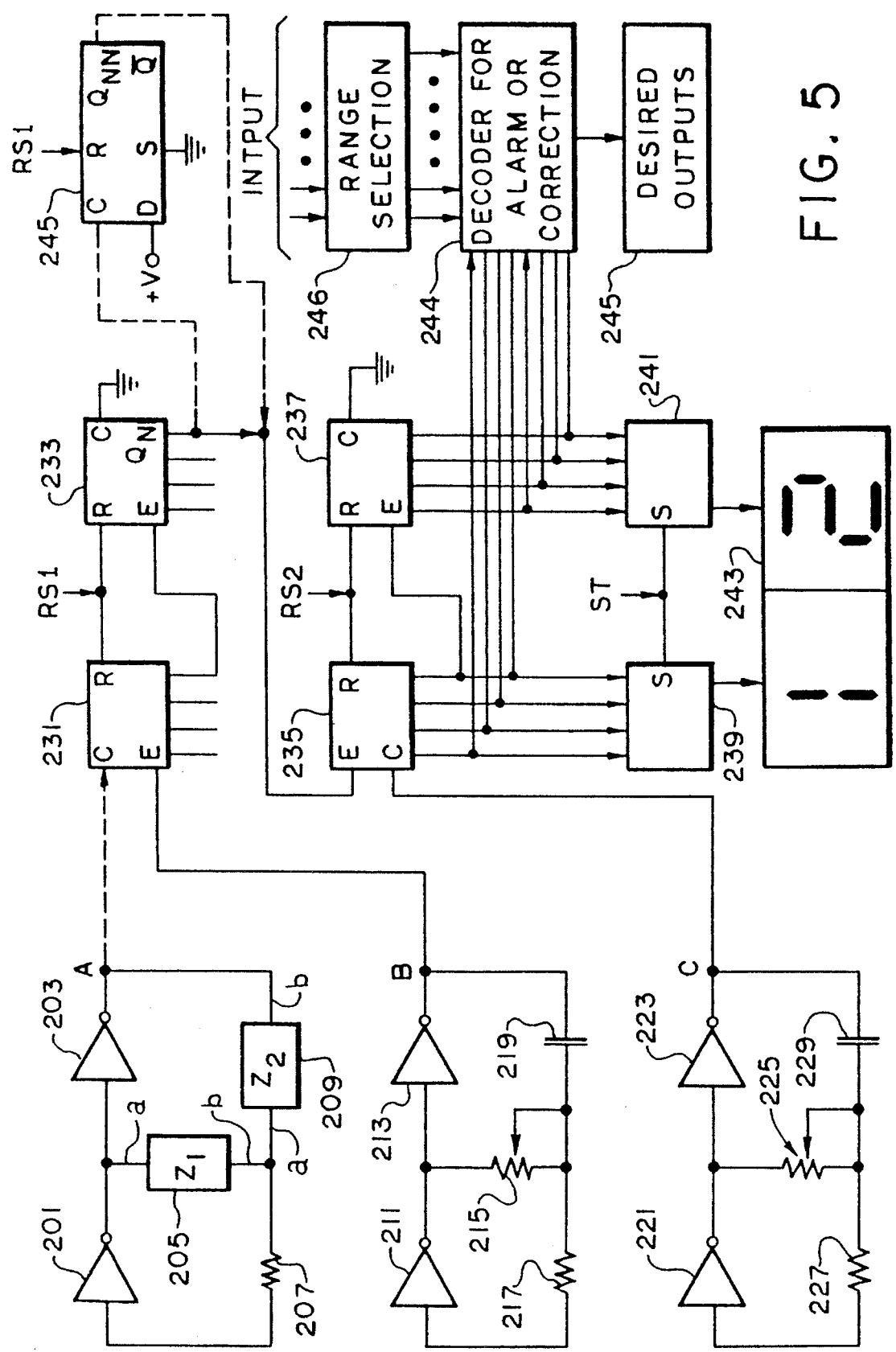
FIG. 5 is a circuit diagram of signal processing circuitry pursuant to an embodiment of the invention which incorporates a CMOS Schmitt trigger logic inverter transducing oscillator for an inductive, resistive or capacitive (i.e., a reactance) sensing signal from a remotely located sensing device.

Turning next to FIG. 5, processor circuitry is shown for detecting variations in frequency, i.e., the repetition rate of a pulse train. FIG. 6 is a timing diagram for explaining the operation of the foregoing circuitry. The processor circuitry of FIG. 5 includes a reactance controlled Schmitt trigger logic inverter network for producing a variable frequency square wave generator or oscillator network whose base frequency is modifiable according to the impedance values of $Z_1$ or $Z_2$, which in turn depend upon the physical displacement of an electrical component thereof to yield an electrical output reflective of such displacement. Such physical displacement is effected through the deflection of the transducer diaphragm 31, 31' and 31" of FIGS. 1–3. It will be recalled that the outputs of the reactance sensor systems of FIGS. 1–3 was the output a, b which is the input a, b of the oscillator network (signal A) in FIG. 5. The processor responds to changes in frequency in this embodiment and yields a numerical display whose magnitude is calibrated to the units of pressure being measured. It should be noted that analog outputs are also possible with the use of the correct counter and D/A convertor, or some form of frequency to voltage conversion, which is one possible method for activating the display of the CPR device shown in FIG. 17B. If the active parameter is resistance or inductance, $Z_1$ is activated and $Z_2$ is fixed: if the active parameter is capacitance $Z_2$ is activated and $Z_1$ is fixed. It is noted that the following description for the processor is the same When the variation of the $Z_1$ or $Z_2$ impedances are caused by the parameter changes of temperatures or light sensitive elements.

A frequency generator is established when the a, b outputs are connected to therein supply the signal in which frequency variation is to be detected. For simplicity and not as a limitation, the circuitry of FIG. 5 is used to describe its operation. For $Z_1$ active, a pair of CMOS Schmitt trigger logic inverters 201 and 203 are connected in series, and $Z_1$, a pressure sensitive variable resistance or inductance or temperature, light or wavelength variable element 205 is connected between the common connection of the inverters and through a resistor 207 to the input terminal of inverter 201. A fixed $Z_2$ capacitance or resistor impedance 209 is connected between the output terminal of inverter 203 and through the pressure sensitive $Z_1$ impedance 205 to the input terminal of inverter 203 and also to resistance 207. If $Z_2$ is a pressure sensitive capacitance $Z_1$ will then be a fixed value of resistance. The output terminal of inverter 203 is designated as point A and the signal present at that point is designated as signal A for convenience of reference. It is to be understood that the variable frequency oscillator shown in FIG. 5 as generating signal A can be replaced by any number of other variable frequency oscillators; however, as described earlier, the Schmitt trigger logic inverter such as the CD40106, or CMOS Schmitt NAND, such as the $CD_{4093}$ will yield benefits in minimal components, low cost and above all, while operating at the same frequency, a lower current by a factor of at least 5 than that seen in the prior art techniques that did not possess the "snap action" characteristics of the device disclosed herein. That is, the non-Schmitt trigger inputs conduct heavily during each transition when the input signal is somewhere between the rail voltages. This is an important consideration for battery operated equipment.

A timing oscillator is constructed similarly, including a pair of inverters 211 and 213 connected in series. The fixed terminals of a potentiometer 215 are respectively connected between the common connection of inverters 211 and 213 and (a) in series through a resistor 217 to the input of inverter 211 and (b) a common connection of the second fixed terminal and the wiping contact through a capacitor 219 to the output terminal of inverter 213. For purposes of explaining the operation of the embodiment, the signal observed at the output terminal of inverter 213 is designated as signal B.

A pulse train generator identical to the timing oscillator just described is provided, but its components can be of different values to produce different pulse widths and repetition rates. That generator includes a pair of inverters 221 and 223, a potentiometer 225, a feedback resistor 227 and a capacitor 229. The output signal at the output of inverter 223 is designated as signal C to aid description of the operation of the circuit.

The output of the frequency generator, signal A, is transmitted through a line connected to a counting means. In the embodiment shown, all of which is disclosed in CMOS for power conservation, the counting means comprises two 4 bit counters, 231 and 233, connected in series to form an 8 bit counter, but the system could have any number of bits for increased resolution. The counter could each be one half of a $CD_{4520}$ binary type circuit. Each 4 bit counter has a count input terminal C, an enable input terminal E, a reset terminal R and four output bit lines. Signal A is transmitted to terminals C of counter 231. The highest count bit line of counter 231 is connected to the E terminal of counter 233. The R terminals of each counter go to a reset line, RS1. The C terminal of counter 233 is grounded and its highest count bit line serves as an output terminal $Q_N$. The output signal B of the timing oscillator including inverters 211 and 213 is connected to enable terminal E of counter 231. When enable terminal E receives a high signal, counter 231 begins counting the pulses in signal A. When that count reaches the sixteenth pulse, meaning 16 pulses have been received, a high to low transition occurs at the highest bit line and so is transmitted to the enable terminal of counter 233 which, serving as a negative edge trigger, counts one unit. The process is repeated until a count of 128 pulses is reached, whereupon the signal at terminal $Q_N$ goes high.

The $Q_N$ terminal of counter 233 is connected to an 8 bit counter driver, including two 4 bit counters 235 and 237 connected to each other as are counters 231 and 233. The enable terminal of counter 235 is connected to the $Q_N$ terminal of counter 233 and the C terminal of counter 235 receives the signal designated as C and generated by the pulse train generator including inverters 221 and 223. Counters 235, and 237 could each be half of a CD4518 BCD (binary coded decimal) type circuit. A reset line RS2 is connected to the reset terminals of counters 235 and 237. The output bit lines of each of counters 235 and 237 are connected, respectively to display drivers 239 and 241 which convert the BCD information into the form necessary to drive a two digit visual display 243. Drivers 239 and 241 each have a store terminal S, both of which are connected to a store line ST, and seven output terminals connected to display 243. Drivers 239 and 241 may each be a CD4056 type circuit if display 243 is of the liquid crystal type in which case a back plane frequency would also be provided for proper operation.

Also, attached to the output bit lines of counters 235 and 237 is a conventional digital decoder 244 to give the desired outputs 245. Connected to decoder 244 are one or more range selectors 246. The outputs may be in the form of a visual, audible or dynamic alarm through an open loop system to inform the user when the measured parameter is inside or outside a preselected range. This feature is especially useful in a CPR device such as the one shown in FIG. 17B because it provides a guideline for an effective range of force to be applied during the CPR procedure. The output may also be in the form of a generated error signal that will automatically make corrections through a closed loop system by increasing or decreasing the parameter being controlled. FIG. 5 also includes, in phantom lines a D-flip flop 245 having its C terminal connected to terminal $Q_N$ of counter 233 (which in this option is not connected to counter 235). A type CD4013 flip flop is suitable for this application. The $Q_{NN}$ output terminal of flip flop 245 is connected to the enable terminal of counter 235. Reset terminal R of flip flop 245 is connected to reset line RS1. As more fully explained below, the purpose of flip flop 245 is to hold or freeze a high signal generated at the $Q_N$ terminal of counter 233, since that signal could assume its low state in the embodiment after 256 pulses of signal A; this would disable the 235, 237 counters causing an incorrect reading to occur.

The operation of the circuit of FIG. 5 is more clearly understood by reference to the timing diagram of FIG. 6 where the top three time scales show the A and B signals and that at terminal $Q_N$ when no stimulus is applied, i.e., when the frequency of the frequency generator is in its initial condition state. If a transducer element is present at $Z_1$ or $Z_2$ in the frequency generator A, that state would be a quiescent one when no force or pressure is being applied to the transducer elements. The middle three time scales show the A and C signals and the signal at terminal $Q_N$ when a positive sense stimulus is applied. The lower three time scales show the timing of the reset and store signals, RS1, ST and RS2, respectively.

At the start of an interval, the timing means of signal B switches to its high condition activating the cycle counter 231, 233 to count the transitions in the pulses generated by the frequency generating means 201, 203. The timing means of signal B switches to its low state and thus, the interval ends on the positive transition of the 128th pulse, i.e., precisely when the $Q_N$ signal goes high, if the frequency generating signal, signal A, is of the constant, quiescent frequency. These conditions are shown in the top three time scales of FIG. 6. The end of timing cycle B generates reset pulse RS1 to clear the counters to zero in preparation of the next measurement interval. Pulses ST and RS2 follow. If a positive sense stimulus is applied causing the frequency of the signal A to increase, the $Q_N$ output goes high before the B signal goes low. This condition is illustrated in the middle three time scales of FIG. 6. In this situation, when the 128th pulse is reached and $Q_N$ goes high, the display driver counter 235, 237 is activated and begins counting the pulses in signal C. This counting continues until the end of the interval when the B signal goes low. The number of pulses of signal C counted is proportional to the increase in the frequency of signal A and, therefore, in the case of a linearly operating transducer element, proportional to the force or pressure applied. As before, the end of timing signal B generates reset pulse RS1 which clears the transducer counters 231, 233 and with $Q_N$ low disables the display counters 235 and 237. The store pulse ST then latches the pulse count of signal C into the display drivers 239, 241 and the information is displayed on digital display 243 and/or through digital decoder 244 as a measure of the magnitude of the stimulus, e.g., the force or pressure applied. Following the ST pulse and the reset signal RS2, the next interval of measurement can begin immediately if desired.

The circuitry of FIG. 5 visually displays a value that is representative of the change in frequency above the base frequency. Each successive display interval shows a value proportional to the difference in frequency above the base value. Circuitry can also be provided to detect changes in frequency having a negative sense, i.e., changes reducing the frequency below the base or quiescent value, and in both the negative and positive sense, analog values are possible.

Figure 5A:
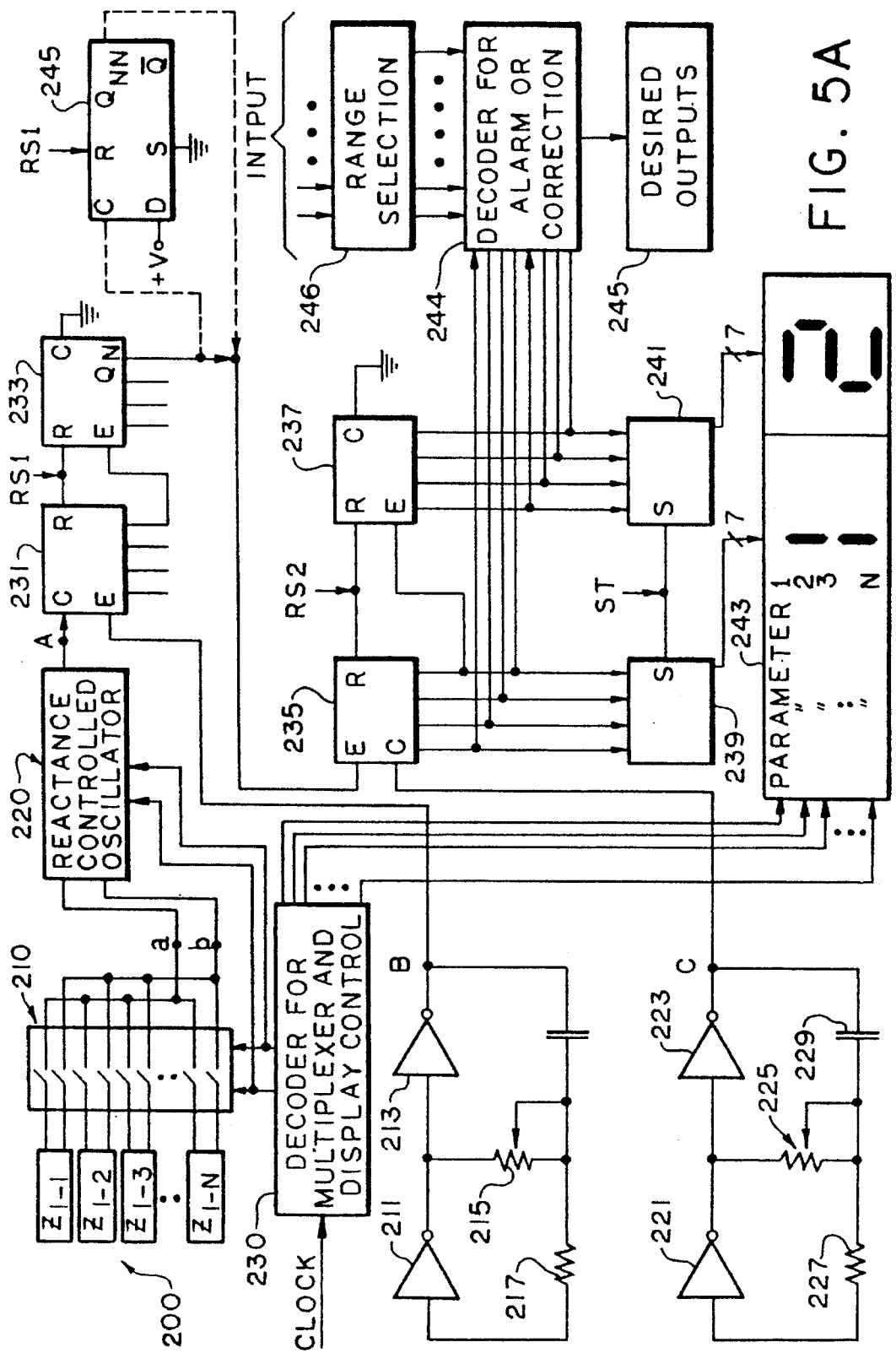
FIG. 5A expands the processor of FIG. 5 to include multiplexing means for multiple inputs from remotely located reactance sensors.
Figure 6A:
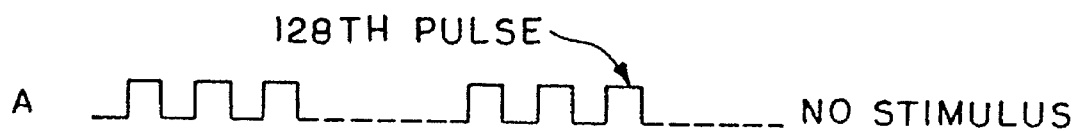
FIG. 6 is a timing diagram for the circuitry of FIG. 5.
Figure 6B:
Figure 6C:
Figure 6D:
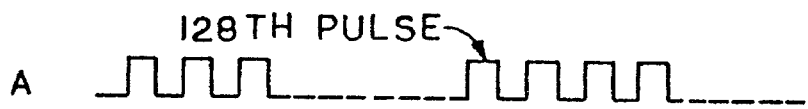
Figure 6E:
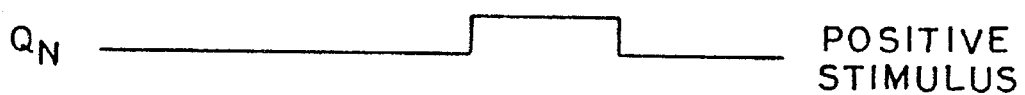
Figure 6F:
Figure 6G:
Figure 6H:
Figure 6I:
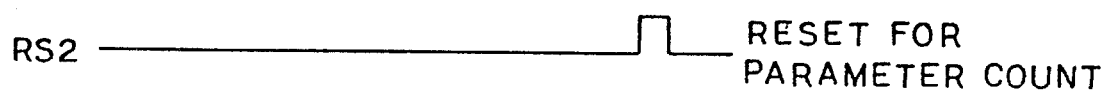

The processor of FIG. 5A illustrates the ability to multiplex a multitude of remotely located sensor signals 200, into a single reactance controlled oscillator. The signals can come from a number of different locations, all of which are measuring the same parameter, pressure for example, or they can include several parameters such as pressure, force, flow, temperature and the like. Therein, the array of sensors 200, connected to multiplexer 210, are selectively switched to the connecting points a, b, of the reactance controlled oscillator 220 for final processing and display as hereinbefore described. Selection of both the switching sequence and associated oscillator sensitivity comes from the encoder and control function 230 and are derived from an appropriate clock frequency shown therein. In addition to the multiplexer and oscillator control signals, decoder 230 also selects the annunciator so that the viewer can tell which of the many parameter values is on the display.

FIGS. 1–3 disclosed various sensor pad techniques. Regardless of which of the pad techniques is used, the processor responds in the same way when pressure is applied.

Figure 7:
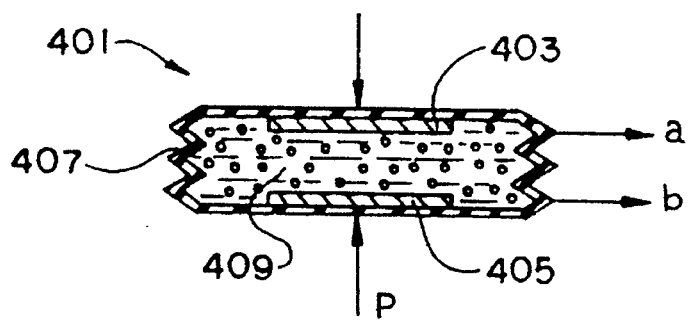
FIG. 7 shows a cross-section of a sensor according to another embodiment of the invention wherein electrical characteristics are varied in accordance with sensed pressure.

The sensor systems of FIGS. 1–3 are mechanical (hydraulic) systems for controlling the electrical response of an electronic circuit through the displacement of a part of a component in that circuit. The invention also includes the direct physical displacement of parts of electrical components to achieve the desired electrical response, either by the movement of fluid from a fluid-filled pad or by the deflection, compression or tension of structure comprising resistant means such as a spring. Referring to FIG. 7, a pad 401 is shown having a flexible wall structure and a pair of conducting plates 403 and 405 on opposite sides of the pad. (Pad 401 can define a closed chamber which is stretchable or otherwise have means for enabling for the displacement of fluid in the chamber). The output Of pat/401 is shown by arrows a, b. Pad 401 is filled with a fluid 407 whose nature depends on the type of component pad 401 is. Fluid 407 preferably saturates a sponge 409 as discussed earlier. When there is no external pressure applied to pad 401, it assumes a relaxed state with plates 403, 405 relatively far apart. When external pressure P is applied, pad 401 is compressed to decrease the separation of plates 403 and 405. When such compression occurs, a change in the internal resistance, capacitance or inductance occurs, which is measured in terms of frequency in the transducer oscillator of FIG. 5. In this case, the pads are totally closed, and pad "thickness" is the actual measuring media; i.e., no escape reservoir for the fluid as described for FIGS. 1–3 is required and there is no transducer diaphragm.

Fluid 407 can be electrically resistive fluid, where the resistance decreases as the separation of plates 403 and 405 decrease. Fluid 407 can alternatively be a dielectric (such as a dry foam or sponge), the capacitance of the pad increasing as the separation of plates 403 and 405 decreases (since $C=\epsilon(A/d)$ where $\epsilon$=dielectric constant, A=plate area, and d=separation of the plates). If a sponge is used, it can be dampened with either a conductive or non-conductive antifreeze liquid or gel to prevent freezing.

Inductive variation is also possible. In this case, a large diameter coil is used so that sufficient inductance is realized in the limited space available if a totally flat pad is an important consideration. In one approach, a thin, but large diameter ferrite slug reacts to increasing pressure by moving into the center of the coil-and vice versa for decreasing pressure. In a second approach, the large diameter coil is actually wrapped on a flat ferrite core and an equally flat "reluctance" shield is moved over or away from the coil. In both cases, the pad provides the return force as the pressure goes down.

It is significant that charged carriers in fluids under the influence of a DC field normally migrate to one or the other of the electrodes depending on the polarity used. It should be noted that this will not occur with the approach discussed herein so long as the frequency signals possess both positive and negative polarities. That is, DC migration is avoided over extended periods of operation because the molecules remain in suspension as they rapidly change their polarized direction with the positive and then negative going field produced by the oscillator. However, both voltages are needed whereas a single polarity is sufficient with the hydraulic approach discussed above.

The sum, average or maximum pressure values as discussed above can also be taken with the type of system shown in FIG. 5. If each pad has its own oscillator, the sum is taken by counting the frequency variation of each in an identical time related succession; the average is found by dividing the sum signal by three, and the maximum by simply letting the pad with the highest frequency enter the processor network; this, of course, assuming that frequency increases with increasing pressure. If not, then the lowest frequency enters the processor.

It should be pointed out that the foregoing is only illustrative of a specific embodiment within the scope of the present invention. As discussed above, other parameter changes, e.g., temperature and light and other forms of radiation or wavelength, may be processed in a similar manner where the detection and displaying of such changes are also intended to be within the scope of the present invention.

Figure 8:
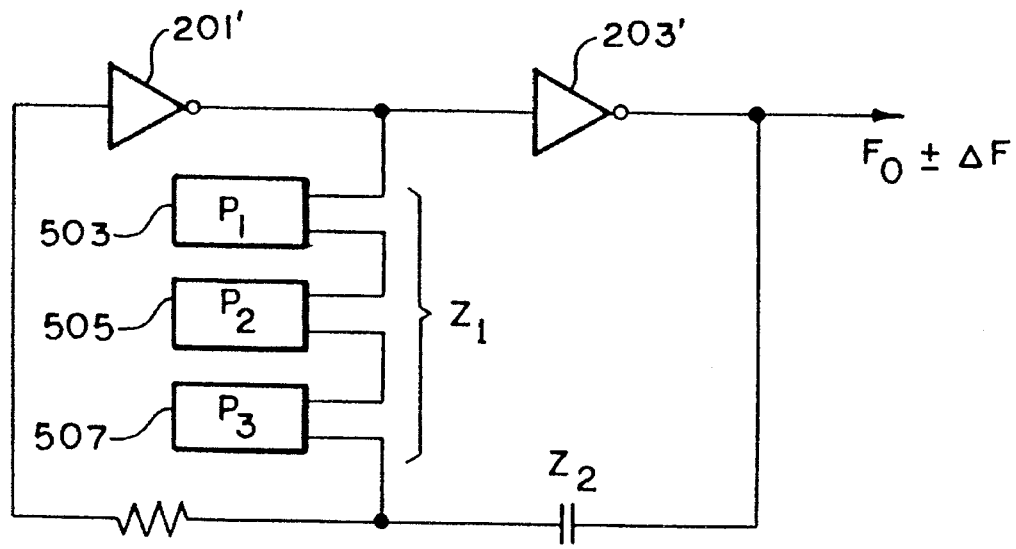
FIG. 8 is a circuit diagram of a transducing oscillator according to the invention, for generating signals corresponding to the sum or to the average value of pressure applied to remote sensors of the invention, where the resistance or the inductance is variable.

Turning next to FIG. 8, an oscillator is shown having inverters 201' and 203' corresponding to inverters 201, 203 of FIG. 5. The $Z_1$ impedance of FIG. 5 is used to detect variations in pads with resistive or inductive interiors, as discussed above with regard to FIG. 7. $Z_1$ of FIG. 7 can be composed of but one component, or a series of components, which is the arrangement shown in FIG. 8. The series-connected pads of FIG. 8 are identified by the numerals 503, 505 and 507, and the pressure applied to them is shown as P1, P2 and P3. The effect on the oscillator frequency A corresponds to the sum of the pressures of N series-connected pads, wherein in FIG. 8, N=3. Because of the effect of changing impedance with changing frequency, a parallel connection of the pads in FIG. 8 is sometimes an advantage as dictated by the application.

Figure 9:
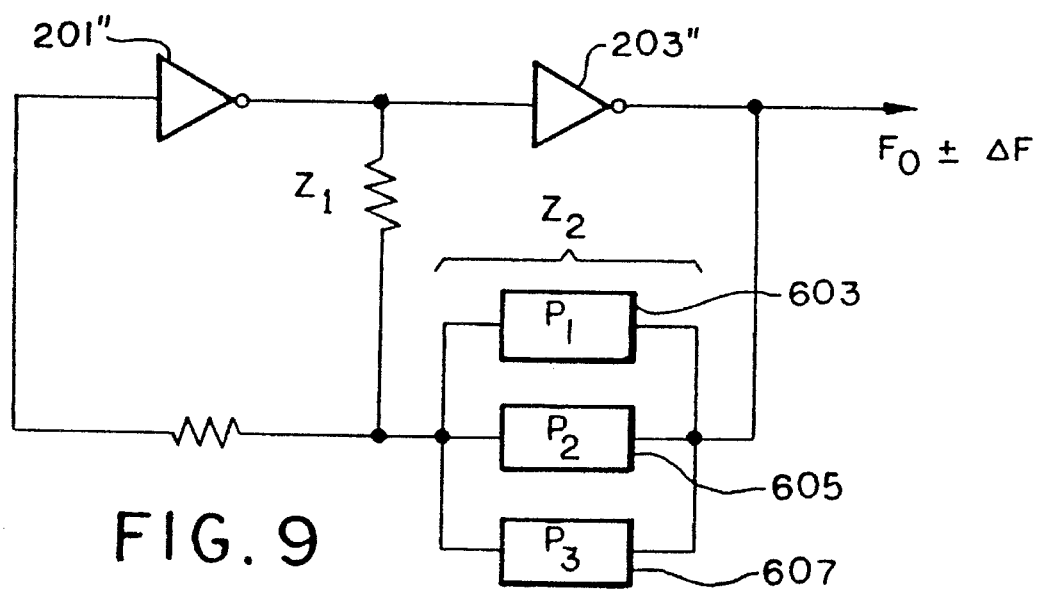
FIG. 9 is a circuit diagram for an oscillator of the type shown in FIG. 8, but where the capacitance is variable.

FIG. 9 shows another oscillator having inverters 201" and 203" corresponding to components 201 and 203 of FIG. 5. In the circuit of FIG. 9, like that in FIG. 5, the $Z_2$ impedance is used for variable impedance values. In FIG. 9, a set parallel-connected pads 603, 605 and 607 have capacitive interiors. Pressures P1, P2 and P3 are applied to the respective pads. Since the capacitance of capacitors connected in parallel are additive, the influence of N pads with capacitive interiors on frequency is also cumulative. Hence, the effect of N capacitive pads is the sum of their capacitances; in FIG. 9, N=3. As explained for FIG. 8, the FIG. 9 network may be better served with a series connection of the pads.

In the arrangements of FIGS. 8 and 9, it is a straightforward matter of obtaining the maximum pressure value. Accordingly, each pad is connected to its own oscillator, and only the pad effecting the greatest change in oscillator frequency is detected, processed and displayed.

In another embodiment of the present invention, another type of sensor according to the invention is illustrated in FIG. 10. This sensor will generate the signal variation directly when the sensor is compressed upon application of external pressure or force. The sensor is a sensor pad or sensing device, broadly identified by the numeral 700, and is made up of supporting means in the form of a semi-stiff upper plate 701 and a lower plate 703. Plates 701 and 703 are held together and their juncture is closed by a seal 702 and a force fit or bonding of springs 707 described below. A coil 705 is fixed to upper plate 701 and coil wires 706 are connected into a processor unit as previously discussed. A movable cap 704 is firmly mounted to the lower plate 703. The two plates are separated by an elastic or biasing means, in this instance, a triangular placement of three springs 707 equidistance around the inner region between the plates is illustrated. In this illustration, when a compressive force is applied, the two plates are moved together and, at the coil/cap interface, a reluctance transducer response is produced. The plates return to their normal static position when the pressure or force is removed. Cap 704 of FIG. 10(A) slides over coil 705 on its core upon application of pressure to the lower plate 703. Reference is made to the reluctance transducers shown in FIGS. 15 and 16 for further discussion of the operation and construction of the transducer of FIG. 10A. Similarly, a resistive or capacitive response may be obtained by incorporating a variable resistance or a conductive or non-conductive, dielectric interface between the two plates. A similar type pad is illustrated in FIG. 7, as discussed above.

FIG. 11 illustrates another embodiment of the sensor pad according to the invention.. The operation of the FIG. 11 sensor is the same as that of FIG. 10 and the corresponding elements are represented as primed numbers. The structure is designed for simplified assembly and is made from a series of inexpensive molded plastic parts, an important consideration for a low cost disposable device. Sensor pad 700' includes an upper plate 701' designed for combination with capsule 708 and cover 709 to therein form a single and unified upper plate prior to coming together with lower plate 703' to form a completed and operational pad assembly. Therein, plate 701' includes a generally cylindrical central vertical wall structure with an annular bead or lip for receiving capsule 708 after coil 705' has first been inserted into the conforming opening and potted into place. Capsule 708 is then inserted into plate 701' after which holding cover 709 is snapped to the conforming ring which serves to hold the three parts firmly together for a unified upper plate. Lower plate 703' is positioned opposite upper plate and is attached to assembled plate 701' by using a set of projections on lower plate 703' and opposing sockets in upper plate 701' to properly locate a set of coil springs 707' between plates 701' and 703' to both hold them together and bias them apart for the static or quiescent no force situation. As indicated above, an inductor coil is encapsulated in capsule 708 to precisely locate it within the housing when upper plate 701' and lower plate 703' are brought together as described. Cap 704', forming part of the inductor network, is inserted into the form fitted opening in lower plate 703' and extends upward through a centrally disposed circular opening in 701'. A sandwich like pressure on lower plate 703' and upper plate 701' then snaps them together by first expanding the conforming lips with finally being held there when they return to normal position when insertion is completed. Thus, a snug, accurate and immovable fit for the critically located components is realized. Finally, an elastomer molded protective cover 702' is installed by simply stretching it over the outer juncture of the two plates. Assembly is fast, accurate, reliable and inexpensive.

The elastic means or material used to maintain the plates of the sensor pads according to the invention in a separated position is not particularly critical where various foam materials, e.g., polymer foams such as polyurethane, sponge, polymeric tubing, metallic prongs, springs, and liquids are used. For the purposes of the embodiment of FIG. 10, the multiple coiled spring arrangement is preferred, but a Bellville washer spring arrangement (not shown in drawing) is also satisfactory. However, a single spring or elastic material may be employed.

The sensors described herein are particularly useful in that they generate electrical output signals (shown as "a–b" in the respective figures) which can be transmitted to remote locations to be read and evaluated. The processor does not have to at the site of the sensor to make use of its electrical output. Signals a–b can be transmitted by electrical wires or transmitted through the atmosphere with appropriate transmission devices to be received by appropriate receivers. In the latter event, the signal is preferably a modulated signal such as one whose frequency is modulated in accordance with the environmental or physical parameter being sensed.

The sensors described above in FIGS. 10 and 11 are preferably "dry" sensors, in that the sensors do not contain a liquid. These sensors have the advantage of remotely sensing the particular environmental or physical parameter change while providing the option of producing the transducer response at the same remote location. Additionally, these sensor embodiments have virtual immunity to changes in altitude and associated problems, an especially important consideration when used with or in an airborne application. While the description of the sensor pads are for compressive forces, it is understood that the electrical response generated by the respective embodiment could be made to occur for tensile forces as well.

The present invention is useful for the remote sensing of various electrical. parameter changes besides force and pressure. Thus environmental or physical parameter changes to which apparatus according to the invention is adaptable to yield an electrical response are pressure, temperature, light intensity and light wavelength or wavelength of some other source of radiation energy. If temperature changes are to be recorded; the sensor, as discussed above, may simply contain air as the fluid as opposed to a liquid wherein the temperature-related expansion provides the pad movement needed to sense the desired change in temperature. The pad may also contain a temperature sensitive resistor. Accordingly, the sensor may contain in place of the pressure sensitive elements illustrated by FIGS. 10 and 11, a light or temperature sensitive resistor. Separate sensors may be connected to the processor circuitry to give the respective outputs or corrections. Multiple signals from each or multiple sensors may be processed by multiple transducer oscillators as illustrated in FIG. 5 discussed above. These multiple signals may be transmitted to a processor unit where one portion of the processor gives the appropriate output for the one signal, e.g., a pressure reading, and the other portion of the processor unit gives the appropriate output for the other signal, e.g., a change in light intensity. In other words, the circuitry illustrated in FIG. 5 may be duplicated to process the separate signals produced as a result of the separate environmental or physical parameter changes. Moreover, these signals may be combined in that at predetermined temperature and pressure values, a separate alarm may be sounded or other output generated. It should be recognized that all the above discussed variations are contemplated and within the scope of the invention.

The systems described above, as previously mentioned, find applicability in pressure measuring networks for use with casts applied to the body. In order to establish a temperature-stable network, a companion system of pads that are exposed to body temperature only, i.e., without the application of pressure, will yield the means for comparison signals in order to compensate for temperature variations of the environment. Also, a temperature sensing pad may be located under the cast along with the pressure sensing pad to alert the attendant if the casting material causes excessive heat for the patient. The two signals may then be multiplexed into the same processor network. By the same token, any number of signals of any parameter variation could be multiplexed into the processor network.

The sensor/transducer apparatus of the present invention may find use in various applications in addition to the ones discussed above. For example, in light of the sensors and apparatus reliability, compactness, sensitivity and relative low cost, these devices may be used to detect pressure changes in pressurized containers. Inert gas pressurized containers are commonly used with analytical instruments, e.g., gas chromatography, and for purging chemical reactions both at a bench scale and production scale. The need for the timely changing of empty containers is evident. However, oftentimes these containers are fitted with mechanical pressure gauges that require frequent visual readings and which also have the potential for failure. Thus, by utilizing a sensing means according to the present invention, a remotely detected parameter change may trigger a visual, e.g., flashing light and/or audible alarm display, which could be quite valuable for indicating the time to install another container. Hence the devices of the invention may find utility in research laboratories as well as in manufacturing plants.

Tire pressure may also be measured where an inexpensive gauge employing a sensing means according to the present invention will yield a fast, accurate and easily read numerical value. Such a reading is normally made on non-moving wheels, however, when reactance sensor of the invention is used, the measurement on a rolling wheel can be taken by allowing the coil and its variable frequency to act as a transmitting antenna. The signal can be detected and processed each time the coil passes the receiver located on the frame of the vehicle.

The devices of the invention may also be used with fire extinguishers to indicate when the extinguisher requires recharging. Such devices are particularly useful for fire extinguishers mounted in chimneys to extinguish chimney fires. Chimney fires are usually caused by the build up of creosote from wood burning installations. Ignition of the creosote is a relatively common occurrence and often gas undetected. Periodic fires of this type progressively damage the chimney structure leading to a potential disaster on an unattended chimney. Thus fire extinguishers have been designed to be mounted in chimneys to extinguish this type fires.

Figure 12:
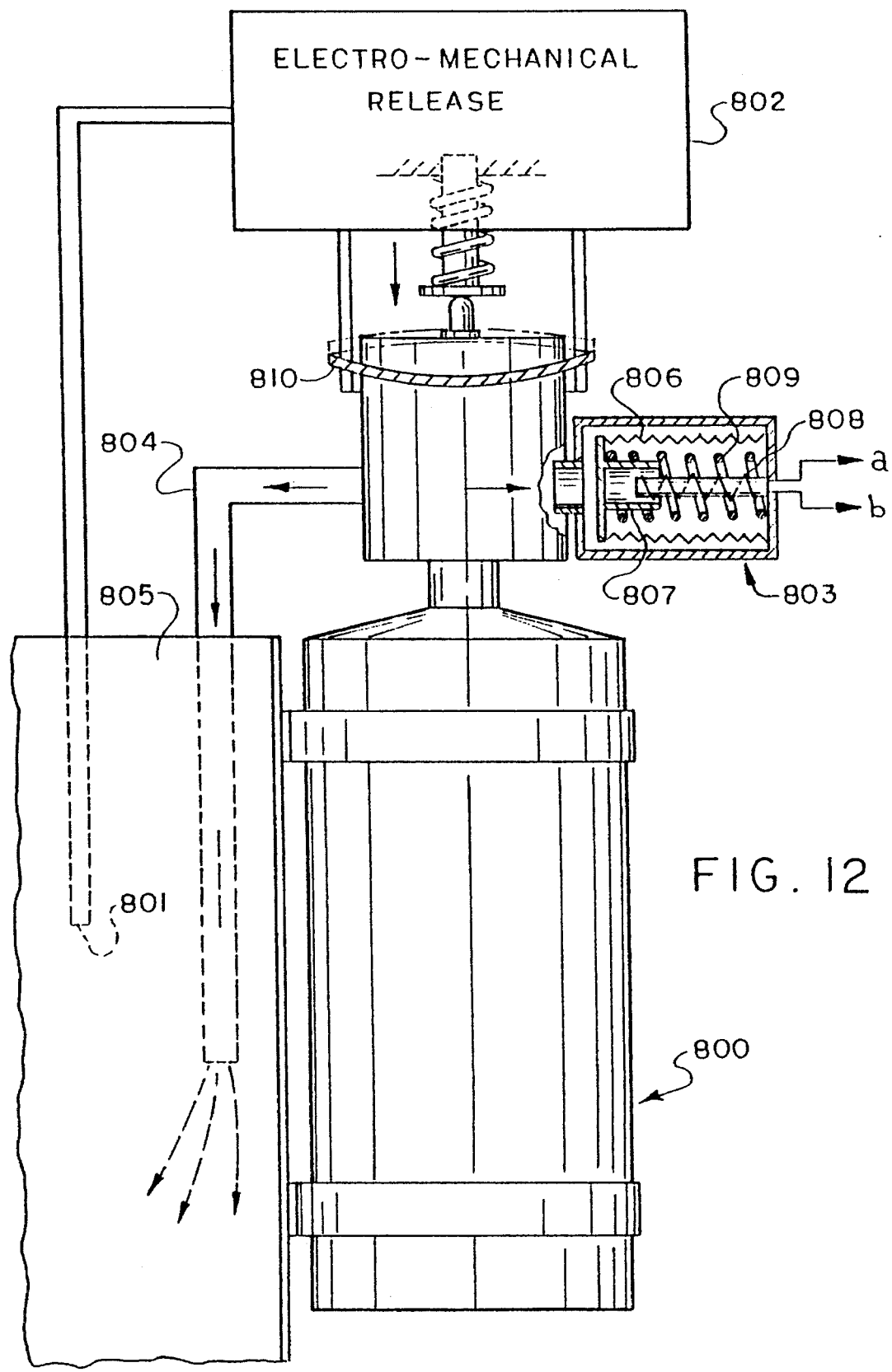
FIG. 12 illustrates a remote sensor according to the invention used in combination with a fire extinguisher.

In the event of a fire, one such fire extinguisher is assembled with a burn link mechanism extending into the chimney that opens when flame is detected and thereby releases a strong spring that sets off the extinguisher, and the fire goes out. This type extinguisher, modified according to the present invention, is illustrated in FIG. 12. The extinguisher is described in greater detail below, and employs a sensor/transducer apparatus of the present invention to indicate when the fire extinguisher requires recharging.

A fire extinguisher 800 in shown which includes a supply tank with a reservoir of fire extinguishing fluid and a fluid release section, and a flame or heat sensitive member 801 connected to an electro-mechanical release 802. The latter is secured to the extinguisher by a strap 810. Release 802 includes a plunger which is biassed in the direction of the illustrated arrow by a strong spring. The plunger is preferably released from a cocked condition by an appropriate release such as a solenoid (not shown) actuable in response to signals from member 801. Extinguisher 800 has a discharge pipe 804 whose outlet is open to a chimney 805, for conveying fire extinguisher fluid from the tank to the chimney. A pressure sensitive sensor 803 for indicating the pressure in the extinguisher tank, communicates with the tank. Sensor 803 is provided in lieu of the known pressure-actuated on-off switch. Sensor 803 includes a bellows 806 having at one end a shield 807 movable with the bellows, and a conductive core fixed on the housing of sensor 803. An inductor coil 808 is provided on the core and includes outputs designated as a–b. A helical return spring 809 biases the bellows to its extended condition.

In use, heat sensor 801 is extended into the chimney 805, either alone or as a back up to the burn link mechanism described above. When dangerous heat or flame conditions occur, member 801 generates a signal reflective of the condition and transmits it to release 802. This signal energizes the solenoid coil to release the plunger in the direction of the illustrated arrow, to actuate an alarm and to effect the discharge of fire extinguishing fluid through conduit 804 into the chimney. The extinguisher and its release mechanism can be of types known in the art. The alarm can be audible and/or visual, and can be displayed at a monitor (not shown) inside the dwelling.

The pressure in the tank of fire extinguisher 802 is shown schematically by the arrow just to the left of sensor 803. When the extinguisher is fully charged, bellows 806 is compressed by a predetermined maximum amount, and shield or cap is likewise telescoped over coil 808 by a corresponding amount. The reluctance signal a–b, which is transmitted to an appropriate monitor, is displayed in an intelligible manner. Even without a deliberate discharge of fluid from extinguisher 800, normal leakage causes a reduction in tank pressure, and this results in the movement of cap 807 to the left under the influence of return spring 806. As cap 806 uncovers coil 808, the reluctance signal a–b changes accordingly. When the tank pressure reaches a predetermined low level, a warning signal such as a blinking yellow LED can be provided to indicate this event. When pressure has been totally released as where the tank has been emptied to extinguish a fire, an immediate refill of the extinguisher is necessary. A blinking red LED is preferably provided and adapted for actuation to indicate this condition. A different audible signal could be provided as well.

For systems according to the invention which are battery powered, a low battery charge may be indicated by a blinking LCD, and a push button test can be provided that sets off a green LED if all is well with the system.

The devices of the present invention may also find use for the remote sensing of acceleration changes for use with automobile safety systems. This is shown in FIG. 13A, where the remote sensing technique is used to control a safety air bag system in a car.

Figure 13D:
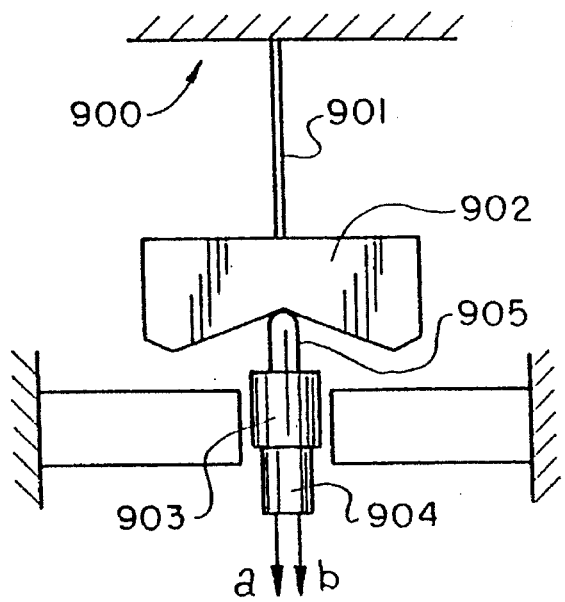
FIGS. 13(D) and 13(E) are schematic views of another acceleration sensing means according to the invention, wherein a mass attached to a pendulum moves part of a sensing device to generate a reactance signal; the views show the embodiment in rest and accelerating conditions.

As shown in FIG. 13D, the remote sensor may be part of a spring-mass system to function as an accelerometer whose signals at the selected levels will result in the actuation of automobile safety systems. The illustrated system detects both linear and angular acceleration in all directions, and the pendulum actuated reluctance sensor of this particular embodiment will react in different ways to different values of acceleration (deceleration). Specifically, a remote sensor 900 comprises a pendulum 901 containing a mass 902, a metallic cap shield 903 having an extension 905, and an electrically conductive wire coil 904. Mass 902 has a cam surface for driving shield 904 downwardly as the mass swings outwardly. A return spring (not shown) moves shield 904 to its initial position as the mass approaches its rest position. With a change in acceleration, the deflection of pendulum 901 results in mass 902 moving against extension 905 of shield 903 to cause the shield 903 to interface with coil 904 to produce an electrical parameter change and a corresponding change in signal a–b shown in FIG. 13(A). For example, at 0.5 G in either axis, the deflection of pendulum 901 will cause the remotely sensed parameter change, and corresponding change in transducer output signal a–b. With the provision of an appropriate processor (see FIG. 5) for processing signals a–b, and the operative connection of the processor to the automobile seat belt restrainer system, the processor signals cause the seat belt restrainer to actuate a motor and gently pull the driver and passenger back to a more comfortable position. A deceleration of 5 G's or more produces proportionately more deflection of pendulum 901, and signifies a high impact crash.

Figure 13E:
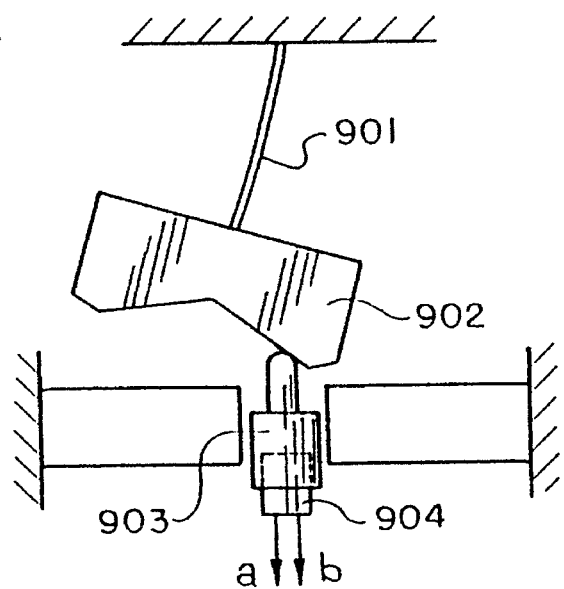
Figure 13F:
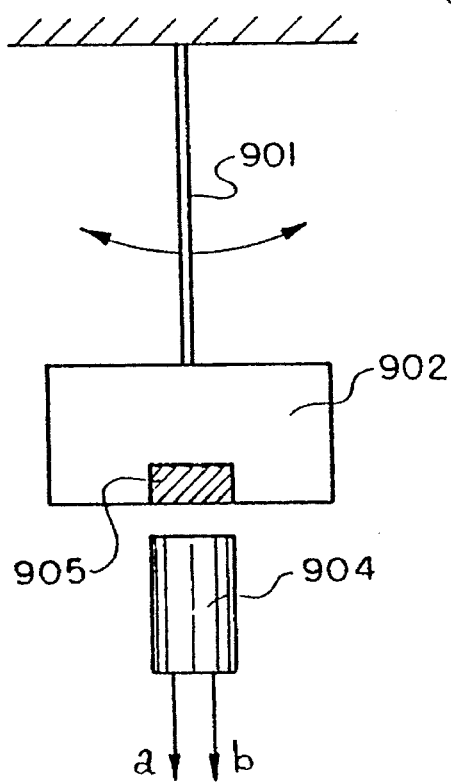
FIG. 13(F) shows a variation on the preceding embodiment where the pendulum carries a permanent magnet.

The system has an air bag release system for releasing an air bag when signal a–b reaches the foregoing 5 G value. It is significant that the reluctance transducer of FIG. 13 can yield measurements of sufficient accuracy to control the timely release of the air bags. Also shown in FIG. 13F is another embodiment of the pendulum/mass approach that is especially useful for the elimination of frictional error, especially in the measurement of small changes in acceleration. In this case, the mass 902 is either a magnet or has a magnet 905 at the interface with coil 904; shield 903 is not necessary in this embodiment. As before, the magnitude of pendulum deflection is proportional to the acceleration; therefore, displacement of magnet 905 causes a corresponding change in the static inductance of coil 904, and the oscillator frequency changes accordingly.

In FIGS. 13B and 13C a single axis device for the remote detection of acceleration is conveniently achieved with a ball, cylinder or other appropriate mass structure enclosed in a tubular restraining structure 910 of FIG. 13B or 920 of FIG. 13C. Dimensions and/or orientation of the tubular structure are in direct accordance with the expected range of the acceleration. Tubes 910 and 920 have end caps with vent holes. Mass structure 911 is located near one end of tube 901, and it may be spring loaded by a return spring 912. Alternatively, the return force can be gravity. Accordingly, tube 920 is situated in an inclined position, and contains a spherical mass 921 which rolls distances in direct proportion to the magnitude of the acceleration. Tube 910 has an inductor coil wound about it, whose output a–b varies according to the position of mass 911 in the coil. Tube 921 has a coil 922 of variable pitch for permitting the continued electrical variation of signal a–b over a greater range as mass 921 moves up the incline at increased acceleration. The reluctance or inductive effect (depending on the mass material) at the a–b terminals will provide the frequency variation referred to in the description of FIG. 5.

The two axis sensor for linear and angular acceleration may be located almost anywhere in the car, however, for a head on crash, a location closer to the front of the car would be an advantage for the most accurate representation of the build up of the acceleration signal. The air bags, of course, are located directly in front of the driver and passenger.

Yet another use in the automotive industry for the devices of the present invention is for engine performance sensors. In modern systems these are described as closed loop systems, but are sometimes used as an open loop indication of engine performance to the operator.

Another industrial application for the devices of the present invention includes use as industrial gas or fluid flow meters, fluid level monitors and the like. Closed or open loop systems may be employed where the sensor is located in the plant and the transducer action is completed at the control room processor where operators may observe and evaluate performance criteria for the plant.

In addition to the medical applications previously discussed, the devices of the invention may be used for spirometers and other respiratory therapy. In FIG. 14A, a pressure sensor 950 is located in the inspiration/expiration air flow path from a patient. While each of the embodiments of FIG. 14 illustrates the reluctance transducer approach of the remote sensor 950, it is understood that the other embodiments of the remote sensor may also be used. As with other embodiments of the invention, the output of the remote sensor is a signal a–b, which can be transmitted to an oscillator device such as the one shown in FIG. 5.

Referring to FIG. 14(B1), 14(B2) an air conduit has a flexible diaphragm 951 extending across it. Diaphragm 951 is shown in FIG. 14(E1), 14(E2) as including a circular peripheral portion and a set of dividers angularly spaced 90° from each other and meeting at a central location. A shield 952 is mounted for movement with diaphragm 951 over a coil 953 wound about a core as described earlier. The foregoing members provide minor obstruction to the air flow produced by the patient. The deflection force on diaphragm 95 1 is proportional to the flow rate and the resulting signal a–b produced according to the extent shield 952 covers coil 953, is processed to indicate the Vital air flow parameters for the patient's condition. The lung force generated by the patient in the absence of air flow is realized by eliminating the flow through path in the diaphragm 951 and simply allowing a deflection in proportion to the force exerted. As before, the electrical parameter change is produced when deflecting diaphragm 951 changes the position of the metallic shield 952 with respect to that of conductive wire coil 953.

In FIG. 14C, a pitot tube 954 in the flow path produces the deflection force. A tube leading from the conduit has a diaphragm 955 extending across it, to which is attached a shield 952 movable relative to coil 953 to yield a processable output signal a–b as described above. The air flow parameter is detected by the force derived from the moving air, while lung force capability is easily obtained by closing off the end of the tube and then allowing the patient to produce a flow-free inspiration or expiration force directly into the conduit. Thus, the patient's lung force causes a deflection of diaphragm 955 to produce an electrical parameter change indicating lung force when the tube is closed off as opposed to air flow and/or volume when the tube is closed off as opposed to air flow and/or volume when the tube is open. In FIG. 14D, a pressure sensor comprising a tube with a venturi section is illustrated for detecting the pressure differential between the throat and exit portions of the structure. A shunt from the throat of tube 956 transmits the air pressure thereat to diaphragm 955, to effect the operation of shield 952 and coil 953 to yield an output a–b as described above. Again, the lung force capability is realized by closing off the end of the tube.

In practice, each patient is assigned their own disposable mouthpiece. To conduct a test, the therapist electrically connects the a–b outputs from the patient's mouthpiece to a hand held processor, display and warning system. The obvious advantage of such an approach is the total isolation from one patient to the next, an especially important feature in view of the present threat of cross contamination from the AIDS virus. None of the earlier developed devices for respiratory therapy can provide this type of isolation; that is, in the prior devices a tube is connected between the patient's individual mouthpiece and the processing unit carried by the therapist. The flow pressure actuates a transducer situated in the unit itself, and while great care is undoubtedly taken to prevent the possibility of cross contamination, a direct link from one patient to the next is nevertheless present.

A few of the vital parameters that can be monitored by the remote sensing spirometer mouthpiece according to the invention are listed below:

1. Total volume of inspiration and/or expiration for each event, and total volume for a selected number of events.
2. Minute volume, the value of air flow generated by the patient in 60 seconds and the number of breaths needed to achieve the minute volume value.
3. Flow rate—instantaneous, average and maximum for each event.
4. Inspiration/expiration respiratory force—instantaneous, average and maximum for each event and the total force—time accumulation for a given period of exercise.
5. Number of events and number of successful events for any of the above that satisfy the preselected goal in terms of range, average, minimum and maximum values.
6. Visual and/or audible signals for achieving the physician's preselected values as selected by way of the patient's condition and/or goals. Mathematical computations can also be made to yield additional indicators for the patient's condition.

The accumulated test results for any number of patients may be stored in a memory unit and later displayed at the discretion of the physician or therapist for further study and/or analysis. With the selection of an appropriate interface, the information may be printed to secure a permanent record for the patient's file.

The electronic sensing, transducing, processing and display techniques disclosed herein are especially applicable to a cardiopulmonary resuscitation (CPR) compression monitor, which heretofore has been a mechanical device. The known device has the external appearance of a device 960 shown in FIG. 17A, although, as explained below, the invention provides an electronic monitoring system designed with CMOS technology. Device 960 (without the inventive electronic circuitry) is of the type sold under the name "CPR Plus" by Kelly Medical Products, Inc. of Princeton, N.J. It has a compression, force-receiving section or chamber 962, which comprises an EDPM-natural rubber compound with a bellows design. Section 962 in the Kelly apparatus holds inert, non-freezing propylene glycol fluid. The top surface 963 is a bonded acrylic pressure plate. The lower surface 964 is contoured to apply force uniformly to the lower sternum. As compressive, repetitive force at a rate of 60 to 100 cycles per minute is applied usually manually to section 962 according to guide 965, the inert fluid is forced by the bellows to rotate a gauge needle 966 clockwise in an arc representative of the instantaneous pounds of force on the delineated scale 967.

Another embodiment of the present invention is shown in FIG. 17B. Here, the fluid-filled section 962 of device 960 is replaced with a dry, transducer system operatively connected to the force receiving, compressible chamber 972. In use, force receiving chamber 972 of device 970 is placed at the patient's lower sternum, and the person administering CPR presses section 972 with a rhythmic downward force at a rate of 60 to 100 cycles per minute to the force shown on display 974 having the legend "CPR Force Indicator."

The display 974 is a radial-type liquid crystal display wherein the display becomes darkened to indicate the instantaneous magnitude of applied force. The force indicated in scale 975 is 75 pounds. A minimum of lines are shown on the drawing for clarity. For improved resolution in the readout, the line count can be increased up to the minimum line spacing available in the LCD technology. (Alternatively, a rectangular bar graph display could be used and would possibly be an advantage for some applications such as a neonatal procedure as discussed with respect to FIG. 20.) Finally, the LCD display can be a back-lighted version so it can be seen when used in darkened situations. Since back lighting would consume greater amounts of battery power, its use could be controlled by a light sensor that would turn the back-lighting on at the appropriate level of ambient light. Back lighting could be particularly useful if the apparatus were used at night after an accident. A light sensor 976 could be used for opening or closing the back light 977 depending on the light detected by photosensor 978.

There are many advantages to the electronic system illustrated in FIG. 17B. For example, the readout gauge is much lighter in weight, is easier to handle and has a thin profile that will avoid interference contact with the patient's chest. Further, the readout gauge is far more rugged and less subject to damage during rough handling in emergency situations, since it lacks a hand for the dial and components for moving the hand. The electronic gauge also does not experience the loss of calibration which occurs with mechanical devices when exposed to high impact or shock.

Because the processor is designed with CMOS technology and the readout is a liquid crystal display, electric consumption is extremely low, therefore, a long battery life is assured. This is especially true when lithium batteries, which are capable of the low-temperature operation under which the device will sometimes be required to operate, are used.

Preselected audible and/or visual cadence signals can also be provided with the electronic system. This feature will provide an easily followed reference signal for a particular patient and/or particular type of physical problem.

Figure 18:
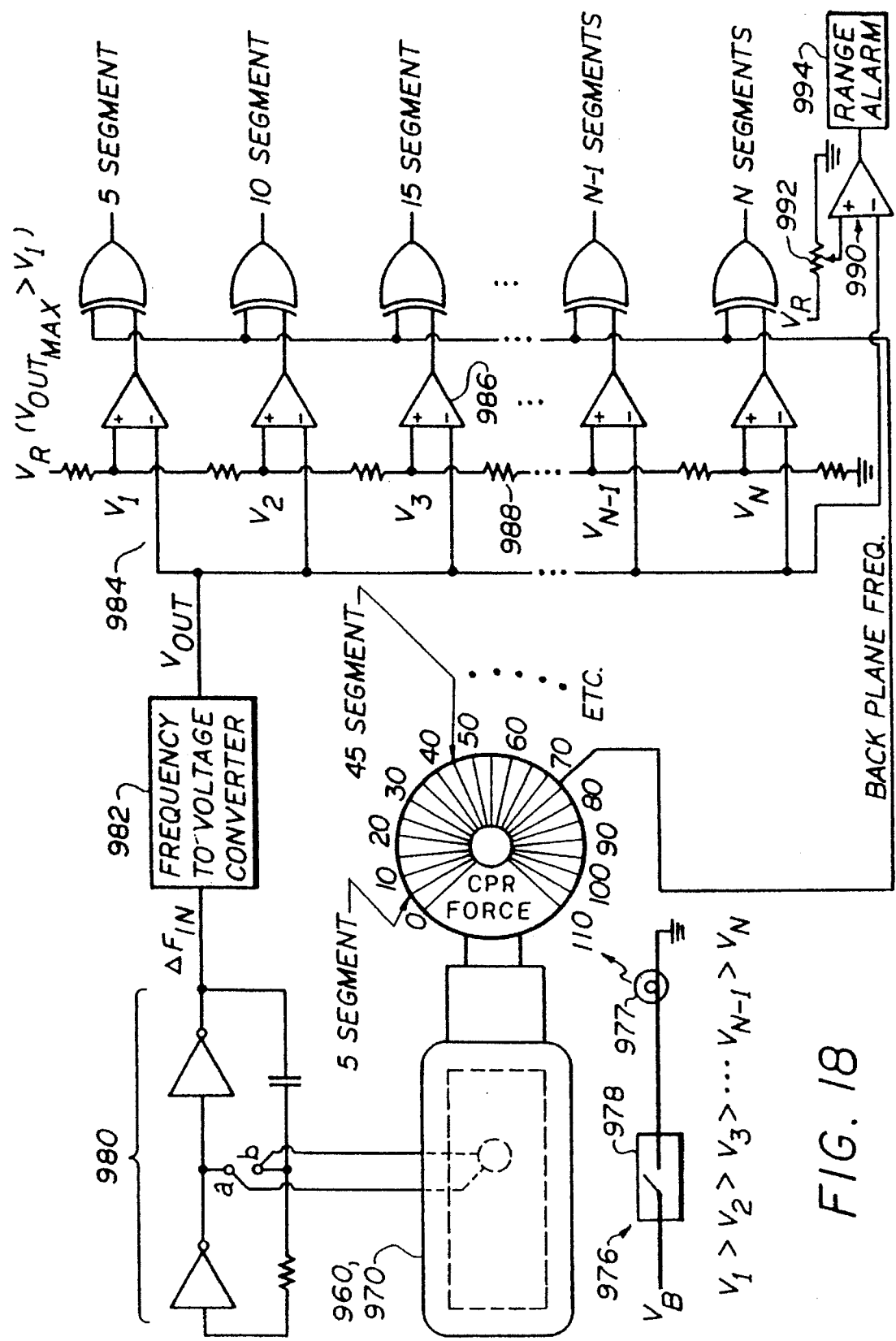
FIG. 18 is a schematic diagram of a preferred embodiment of the circuitry and processing elements used to generate the real time display of applied force to the CPR device depicted in FIGS. 17A and 17B.

FIG. 18 is a schematic diagram illustrating a simple method for displaying the real time force of the CPR device 960 shown in FIG. 17A, and CPR device 970 shown in FIG. 17B. For this example, the output frequency of force-dependent oscillator 980 will increase with increased force. The frequency signal is applied to a frequency-to-voltage converter (FVC) 982 which provides a smoothly decreasing DC voltage at 984 as the frequency increases in response to increasing applied force. In its simplest form, the FVC can be a standard low pass filter comprising a sufficient number of stages to provide a strong and smooth voltage variation.

Figure 19:
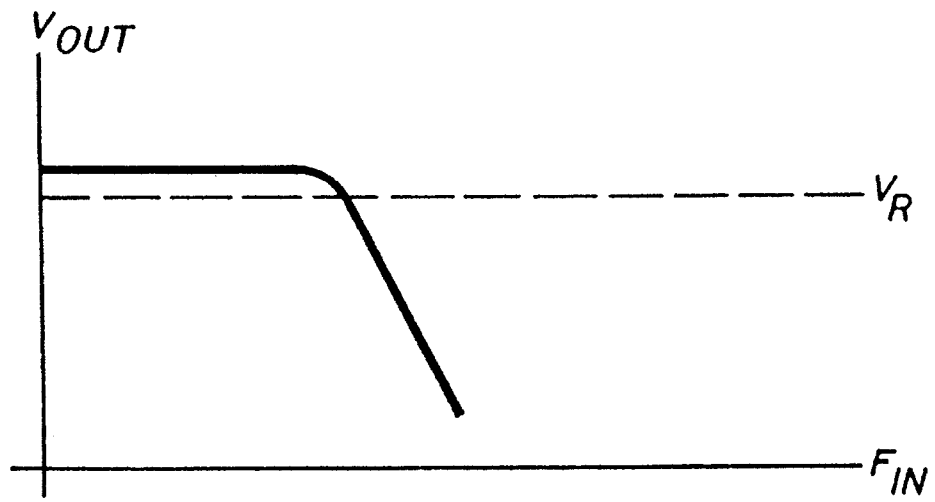
FIG. 19 is a graph of voltage versus force, for part of the circuitry shown in FIG. 18.

The decreasing voltage, as shown in view FIG. 19, is applied to the respective negative ports of a long string of comparators, 986, all residing in a single custom integrated circuit which produces a low cost, low power, compact design. Each of the positive ports from the comparators go to different locations on a long chain of divider resistors 988 which are driven by a stable and fixed reference voltage $V_R$.

The voltage values along the resistor chain will decrease at each position as the chain moves toward ground. In the case when no force is applied, all of the comparator outputs are low because the frequency is at its lowest value and the voltage at 984 is at its highest value. As the frequency increases in response to increased applied force, the voltage at 984 decreases; therefore, the positive ports will successively become more positive than the $V_{OUT}$ value at the negative port. When the positive port of a particular comparator becomes more positive than the $V_{OUT}$ value, the comparator output value switches to a high state. Each comparator output goes to an exclusive OR gate that will serve to change the phase of the frequency signal on the LCD segment. When the segment frequency is out of phase with the backplane frequency, the segment becomes active and the shaded area of the display progressively enlarges with increasing force. A range alarm comparator 990 can be incorporated having a negative input connected to the voltage at 984 and a positive input connected to potentiometer 992 having the reference voltage $V_R$. The setting of the potentiometer determines when a range alarm 994 is activated. When the applied force goes high enough, the voltage on the comparators goes low enough, and range alarm 994 is activated. The alarm could be visual or audible. For children or infants, the alarm would go off when a force greater than a low force were exceeded, whereas the potentiometer would be set for higher force values for adults.

Figure 20:
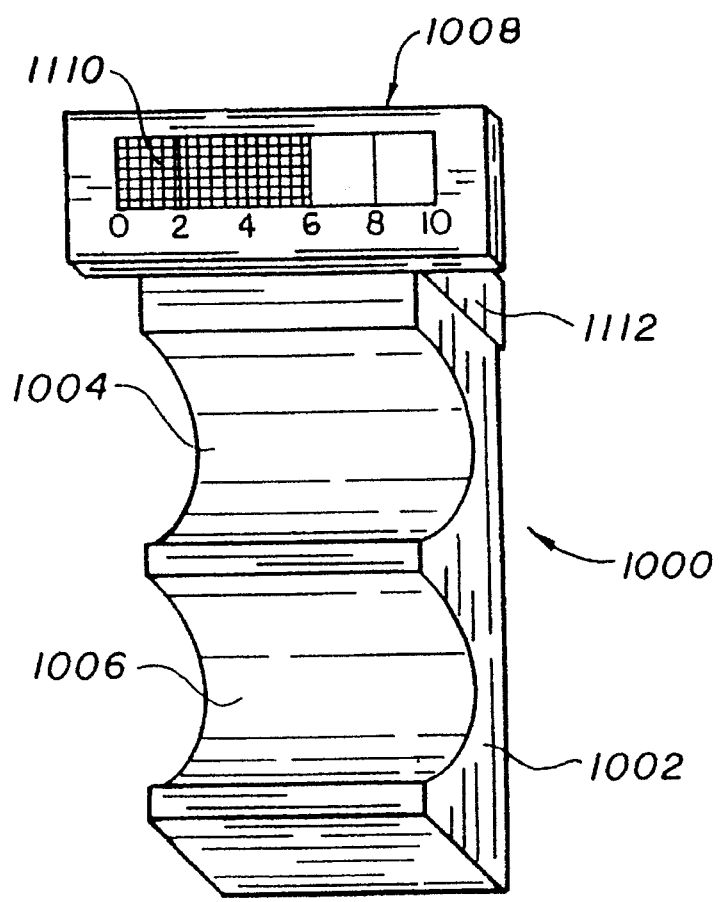
FIG. 20 is a perspective view of a neonatal device according to the invention.

A related CPR compression monitor is shown in FIG. 20. Here, a neonatal CPR compression monitor or device 1000 is illustrated. Device 1000 has a force receiving section 1002 which is similar to sections 962 and 972 of FIGS. 17A and 17B, and incorporates the circuitry of FIG. 18. However, it has finger supports 1004 and 1006 for receiving the two main fingers of the user's hand. Device 1000 is placed on a baby's sternum, and the user applies digital pressure to supports 1004 and 1006, and device 1000 transmits that pressure to the baby's chest. A display 1008 has an LCD bar graph 1110 displaying the amount of pressure applied, which is shown in FIG. 20 as 6 pounds. Device 1000 could only be used effectively with infants. As with FIGS. 17A and 17B, it could have a range alarm comparator. Device 1000 is effective because it is small enough to fit on a baby's sternum, it is lightweight, and it can be used with only two fingers. A cadence device 1112 provides reference signals to enable the user to maintain a proper CPR compression rate.

The display could also be driven with a microprocessor which repeatedly counts cycles from the force dependent oscillator. The time intervals for these count sequences would have to be short enough to assure a virtual real time readout of the applied force. The count value of each interval would address a corresponding ROM location which, in turn, would activate that specific segment of the display. Upon the release of the force, each of the signals would be reset prior to activating the display segments for the next application of force.

A phenomenon that occurs during space travel or as a result of gravitational changes during flight is the redistribution of body fluids. Presently, to determine the redistribution of body fluid during such gravitational changes, the measurements are made with a tape measure of changes in the circumference of a limb. A sensing device pursuant to the present invention allows a more precise, continuous and early method for measuring redistribution of body fluids during space flight or while the body is being subjected to a constant or frequent change in gravitational forces.

Another embodiment with the scope of the present invention is the use of a thin profile pressure sensitive pad or form fitted pressure sensitive glove to facilitate the monitoring and display of the pressures applied in the course of corrective osteopathic or chiropractic realignment. This application is beneficial for treatment of patients suffering from such maladies as polio and spina bifida, as well as many other orthopedic and osteopathic problems.

Aside from the examples given above, the device of the present invention may find use for portable or fixed blood pressure instruments, jet inoculators, electronic ski bindings, running shoes, golf clubs and many other impact related sport activities such as baseball, football, basketball, karate, boxing and the like.

The invention has been described with particular emphasis on the preferred embodiments, but it should be understood that variations and modifications within the spirit and scope of the invention may occur to those skilled in the art to which the invention pertains.

What is claimed is:

1. A force sensing system for generating a intelligible output signal corresponding to a parameter, said system comprising:

sensing means having a stationary first portion and a second portion movable relative to the first portion for generating an electric reactance signal corresponding to the parameter;

first supporting means connected to a housing or conduit for supporting said first portion of said sensing means;

second deflectable supporting means for supporting said movable second portion of said sensing means;

securing means for securing said first and second supporting means in a movable relationship, said first and second supporting means being movable relative to each other in response to the occurrence of said parameter to move said movable second portion with respect to said stationary first portion of said sensing means to generate said electric reactance signal;

processing means including reactance controlled square wave generator means for receiving said reactance signal and for generating a corresponding variable period pulse train transduced signal, voltage converter means for establishing a voltage signal having a magnitude proportional to the frequency of the variable period pulse train transduced signal, and means for receiving said voltage signal and generating an intelligible output signal reflective of the magnitude and variation in said voltage signal; and transmitting means for transmitting said electric reactance signal from said sensing means to said processing means.

2. A force sensing system for generating an intelligible output signal corresponding to a parameter, said system comprising:

sensing means having a stationary first portion and a second portion movable relative to the first portion for generating an electric reactance signal corresponding to the parameter;

first stationary supporting means connected to a housing or conduit for supporting said first portion of said sensing means;

second deflectable supporting means for supporting said second portion of said sensing means for movement relative to said first stationary supporting means in response to the occurrence of said parameter, to move said second portion to generate said electric reactance signal;

processing means including reactance controlled square wave generator network means for receiving said reactance signal and for generating a corresponding variable period pulse train transduced signal, voltage converter means for establishing a voltage signal having a magnitude proportional to the frequency of the variable period pulse train transduced signal, and means for receiving said voltage signal and generating an intelligible output signal reflective of the magnitude and variation in said voltage signal; and transmitting means for transmitting said electric reactance signal from said sensing means to said processing means.

* * * * *